United States Patent [19]

Stormo

[11] Patent Number: 5,531,897
[45] Date of Patent: Jul. 2, 1996

[54] DYNAMIC BED REACTOR

[75] Inventor: Keith E. Stormo, Moscow, Id.

[73] Assignee: Idaho Research Foundation, Inc., Moscow, Id.

[21] Appl. No.: 960,963

[22] Filed: Oct. 13, 1992

[51] Int. Cl.⁶ .................................. C02F 3/00; C02F 1/28
[52] U.S. Cl. ...................... 210/606; 210/631; 210/632; 210/672
[58] Field of Search ..................................... 210/601, 606, 210/610, 611, 615–618, 631, 632, 662, 663, 672, 679, 692

[56] References Cited

U.S. PATENT DOCUMENTS

| | | | |
|---|---|---|---|
| 4,181,604 | 1/1980 | Onishi et al. | 210/615 |
| 4,416,993 | 11/1983 | McKeown | 210/611 |
| 4,419,243 | 12/1983 | Atkinson et al. | 210/618 |
| 4,634,672 | 1/1987 | Baumgarten et al. | 435/182 |
| 4,715,958 | 12/1987 | Fuchs | 210/616 |
| 4,746,435 | 5/1988 | Onishi et al. | 210/615 |
| 4,833,081 | 5/1989 | Walker | 435/182 |
| 4,997,753 | 3/1991 | Dean, Jr. et al. | 435/170 |
| 5,039,414 | 8/1991 | Mueller et al. | 210/610 |
| 5,100,783 | 3/1992 | Dean, Jr. et al. | 435/176 |
| 5,116,506 | 5/1992 | Williamson et al. | 210/610 |
| 5,217,616 | 6/1993 | Sanyal et al. | 210/617 |

FOREIGN PATENT DOCUMENTS 3530322  5/1986  Germany.

OTHER PUBLICATIONS

Partial English language translation of German Patent No. 3 530 332.

*Primary Examiner*—Thomas Wyse
*Attorney, Agent, or Firm*—Klarquist Sparkman Campbell Leigh & Whinston

[57] ABSTRACT

A dynamic bed reactor is disclosed in which a compressible open cell foam matrix is periodically compressed and expanded to move a liquid or fluid through the matrix. In preferred embodiments, the matrix contains an active material such as an enzyme, biological cell, chelating agent, oligonucleotide, adsorbent or other material that acts upon the liquid or fluid passing through the matrix. The active material may be physically immobilized in the matrix, or attached by covalent or ionic bonds. Microbeads, substantially all of which have diameters less than 50 microns, can be used to immobilize the active material in the matrix and further improve reactor efficiency. A particularly preferred matrix is made of open cell polyurethane foam, which adsorbs pollutants such as polychlorophenol or o-nitrophenol. The reactors of the present invention allow unidirectional non-laminar flow through the matrix, and promote intimate exposure of liquid reactants to active agents such as microorganisms immobilized in the matrix.

28 Claims, 10 Drawing Sheets

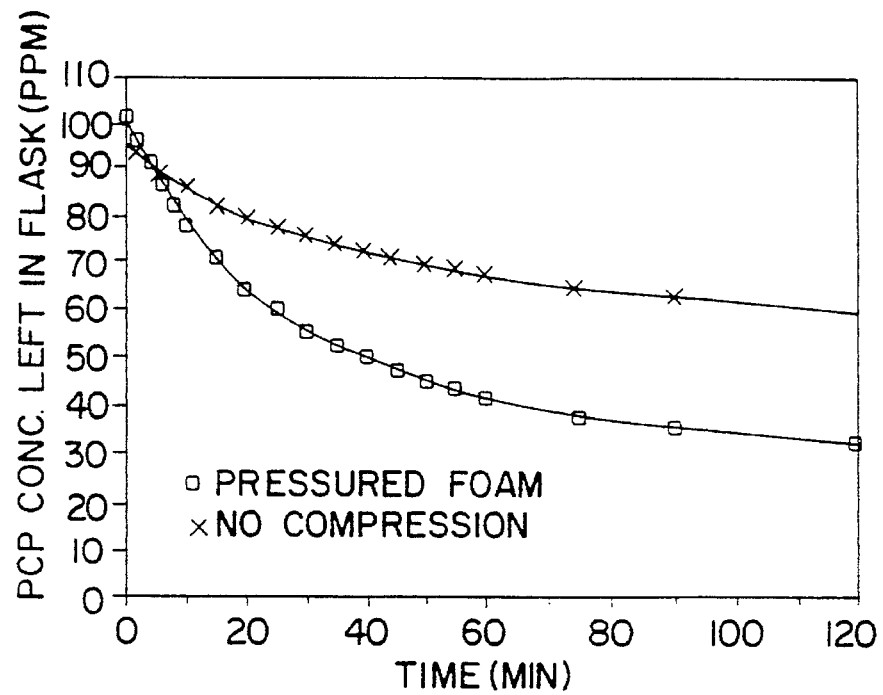
FIG.3
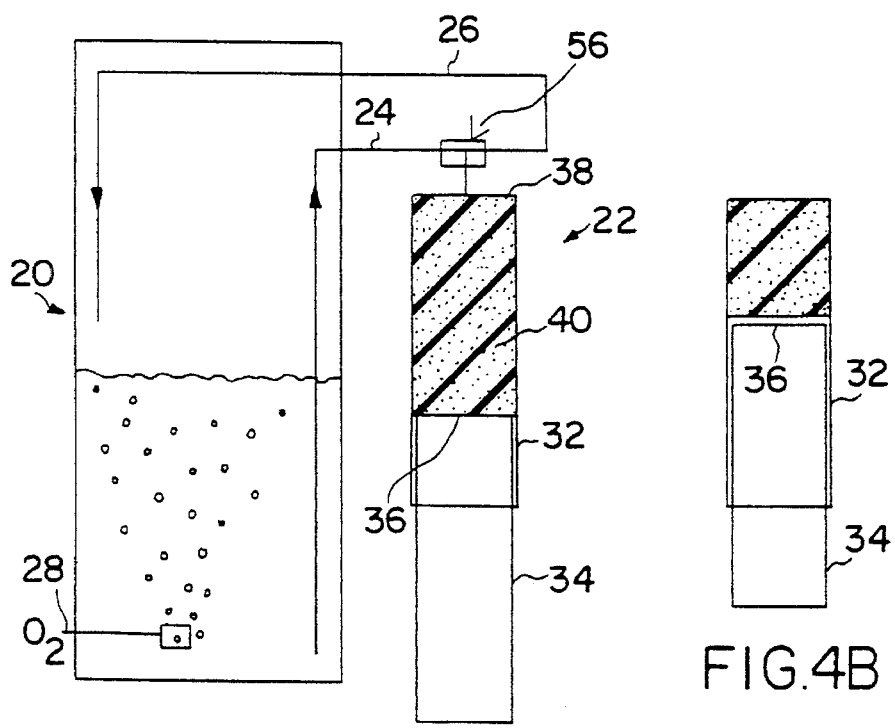
FIG.4A
FIG.4B

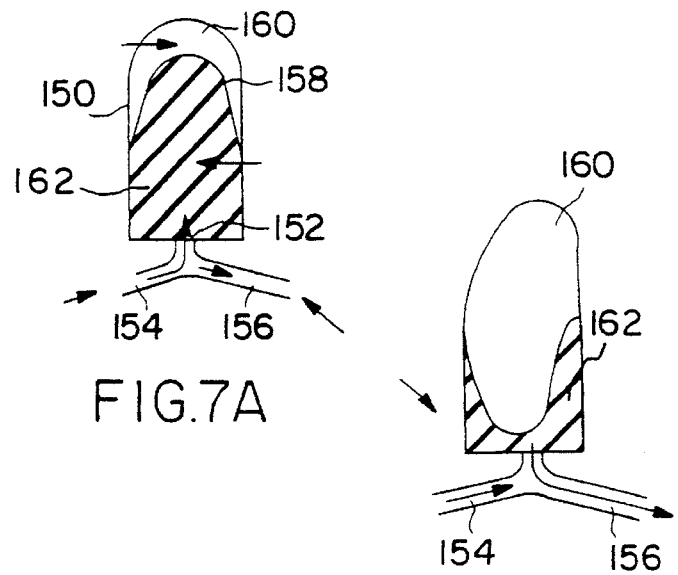
FIG.7A
FIG.7B
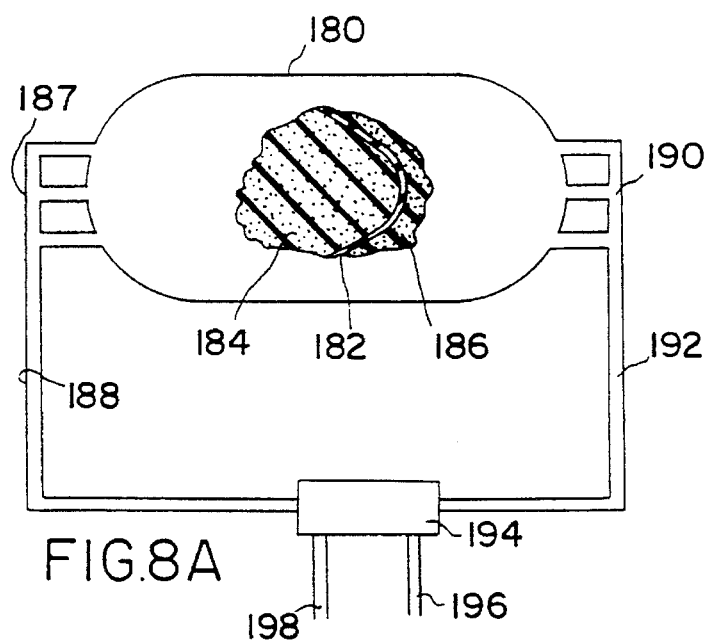
FIG.8A
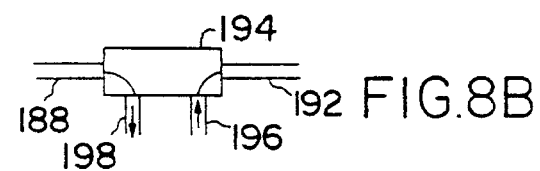
FIG.8B
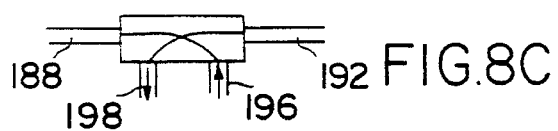
FIG.8C

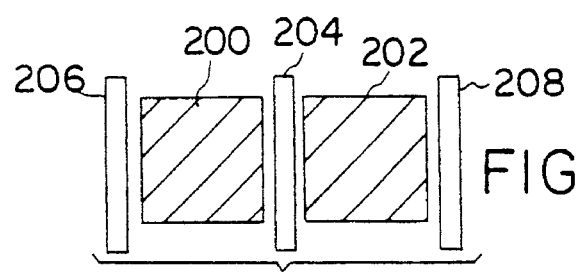
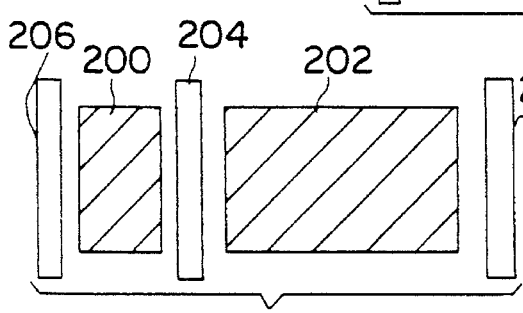 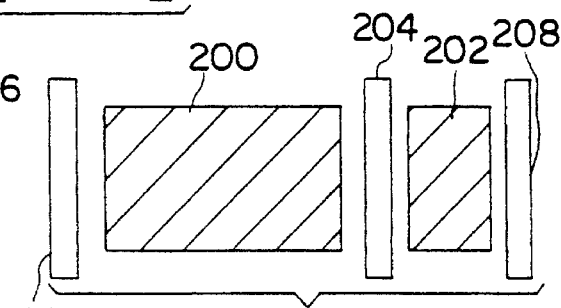
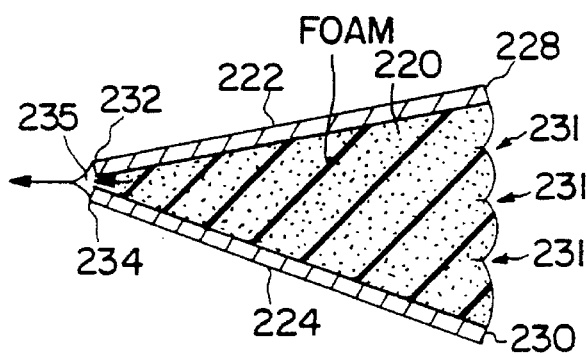
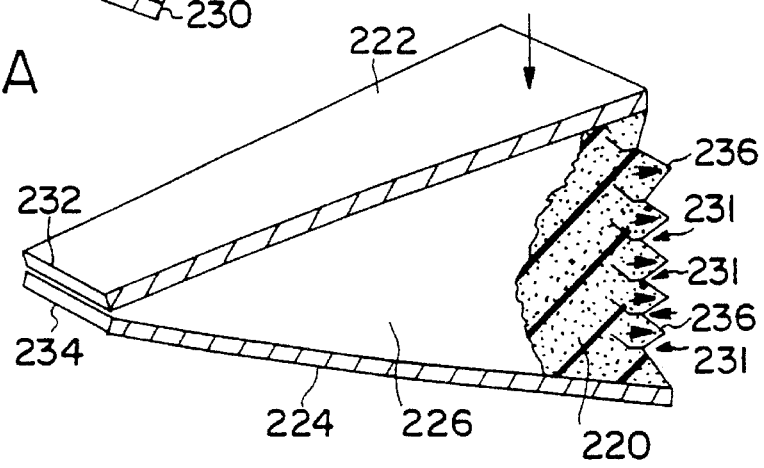

DYNAMIC BED REACTOR

ACKNOWLEDGEMENT OF GOVERNMENT FUNDING

The microbeads developed by the present inventor and described herein were developed under U.S. Department of Energy grant no. 07-89ER60847-000. The government may have certain rights in that aspect of the invention. The remainder of the work described herein was not performed with federal grant funding.

BACKGROUND OF THE INVENTION

1. Field of the Invention

This invention concerns a chemical reactor, particularly a bioreactor in which a reactive matrix adsorbs or biochemically reacts with solutes in a liquid.

2. General Discussion of the Background

Biological reactors have been developed that use immobilized microorganisms or enzymes to degrade pollutants. Examples are found in U.S. Pat. Nos. 4,181,604; 4,416,993; 4,746,435; and 5,116,506, wherein microorganisms are grown in biofilm layers on permeable membranes. The microorganisms in the biofilm transform or degrade pollutants as polluted liquid passes through or parallel to the membranes and comes into contact with the organisms. Unfortunately, the membranes provide limited surface area on which the microorganisms can grow, and diffusional limitations into the biofilm reduce the efficiency of the reactor. Only microorganisms near a surface of the film have sufficient access to nutrients and pollutants to efficiently degrade pollutants and other biological substrates. Such reactors normally have a low biocatalyst density, and the volume of substrates that can be degraded in any given period of time is limited.

Other bioreactors have attempted to solve this problem by suspending microorganisms on small particles that are fluidized in a reactor. A higher mass transfer between the liquid and the particle surface can be achieved with such a design, but the fluidized particles distribute unevenly throughout the reactor. Uneven particle distribution leads to less than optimal utilization of the total available reaction volume in the reactor, and mass transfer limitations between the surface of the particle and the interior often occur. Very small particles also tend to flow out of the reactor as process fluid is exhausted. U.S. Pat. No. 4,833,081 attempted to improve particle retention in the matrix by incorporating, into a polyurethane foam support, small beads that contained microorganisms. The beads were suspended in the polyurethane foam to provide a fixed bioactive matrix through which a process liquid could pass. Optimum reactor volume was still not obtained, however, because diffusional limitations in the beads, and in foam containing the beads, inhibited vigorous growth of organisms within the interior of the bead. Channeling would also be likely to occur in areas of the foam with less restricted flow.

Beads that contain biological cells in U.S. Pat. No. 4,833,081 are described as having a diameter in the 50–2000 micron range. These beads are large enough that in many cases they provide diffusional barriers to the exchange of substrates and nutrients with the process liquid. The beads in that patent are also formed by an oil emulsion process that covers the bead with oil as it is formed. The bead must be washed free of the oil before it can be used in a bioreactor. Oil emulsion or interfacial polymerization processes have been thought essential to form beads of smaller than 100 microns diameter. Other processes have been found to produce even larger beads that have more serious diffusional limitations. Yet no process has been able to produce microbeads, especially with living cells, in which substantially all the beads have diameters less than 50 microns.

Another bioreactor is shown in German Patent 3 530 332, which discloses a slow moving anaerobic plugged flow type bioreactor for degrading sewage. This upflow reactor contains a series of cylindrical sponges that span the cross-section of the reactor. Slow growing microorganisms fixed on the surfaces of the sponges provide a biomass that anaerobically degrades sewage. The sponges are compressed only 0.05 meters about once per minute to dislodge small air bubbles from the surfaces of the sponges before the small bubbles coalesce to form large bubbles that disrupt reactor flow. During compression, liquid flows out of the sponges in both an upflow and downflow direction. Hence a significant portion of the liquid expelled from the sponge flows back into the sponge, which diminishes efficient transfer of reacted liquid out of the sponge.

Yet another drawback of previous reactors has been their reliance on external pumps to move liquid into and out of the reactor. The German Patent, for example, relies on a superimposed process flow through the reactor that is only periodically interfered with by compression of the sponges. Liquid will not move through the reactor in the absence of external pumps forcing a flow through the bed.

It is accordingly an object of this invention to provide an improved reactor in which the reactor itself is designed to provide a pumping force, without relying on external pumps to move liquid through the reactor.

Another object of this invention is to increase the non-laminar flow inside the reactor to more uniformly mix the new liquid with the old liquid and contact all of the reactive material in the reactor with this new solution.

Another object of the invention is to provide an improved reactor that more fully takes advantage of the available volume in the reactor to achieve biological transformations or other reactions.

Yet another object of the invention to provide an improved reactor that can more effectively perform sequential reactions, and monitor and control reaction parameters to optimize the reactions in the system.

Even yet another object is to immobilize biologically active materials in a reactive matrix without imposing significant diffusion barriers between the biologically active materials and a process liquid in the reactor.

Finally, it is an object of this invention to provide biologically efficient microbeads that can be manufactured by a simple process that does not require oil immersion.

SUMMARY OF THE INVENTION

The foregoing objects are achieved by providing a method of transporting a liquid through a reactive or adsorptive matrix in a dynamic bed reactor. The matrix is made of a resilient compressible open cell foam material such as polyurethane. A liquid held in the matrix contains reactants or adsorbates which undergo a reaction in or are adsorbed in or to the matrix. The foam matrix is periodically compressed to expel a first sample of the liquid from the matrix, and the resilient matrix is subsequently allowed to expand and draw a second sample of liquid into the matrix. The liquid that is drawn into the matrix is substantially free of the liquid that was expelled from the matrix in an immediately preceding compression step. Excellent mass transfer of liquid therefore occurs through the matrix with each cycle of compression and expansion. There is also a high degree of non-laminar flow during each cycle that provides excellent mixing in the matrix. This non-laminar flow can be readily varied depending on the degree of shear sensitivity in the reactor for the particular matrix, reactants or immobilized biological material.

In preferred embodiments, the matrix contains a bioactive material such as an enzyme, a biological cell, or a combination of biological cells and enzymes. The bioactive material is immobilized in the matrix, and biochemically transforms the reactants while they reside in the matrix. The enzymes or cells may be covalently or ionically bound to the matrix, or may instead be placed in beads immobilized in the matrix. Matrix immobilization of the bioactive material allows the flow reactor to operate at much higher flows than could otherwise be used because the beads are not swept away by the flow of liquid through the reactor. Immobilization in the beads increases cell loading capacity, enhances rates of production of microbial products in the reactor, and in many cases increases the stability of the bioactive material and its useful life.

In one particular embodiment, substantially all the beads have diameters less than 50 microns. The small size of these beads promotes diffusion of oxygen, nutrients, reactants and products, and allows substantially the entire volume of the bead to be used for microbial growth. Beads that are significantly larger tend to allow microbial growth only near the bead surface, and diminish effective reactor volume. Prior methods of making beads with immobilized living material have been unable to consistently produce beads having diameters less than 50 microns, and have therefore been unable to take advantage of the benefits of the microbeads of the present invention. Such large beads also increase expense because they require greater amounts of expensive bioactive material that is not active. The microbeads of the present invention are made by ultrasonic droplet formation and subsequent solidification, which allows the beads to be made easily in large amounts, without the necessity of oil immersion or interfacial polymerization.

A particularly useful method of microbead formation has been found in which the microbeads are formed without oil immersion or interfacial polymerization. The microorganisms, enzymes, or other desired material is distributed in an immobilization material such as alginate, agar, carrageenan, or polyacrylate, having a viscosity greater than 100 cp. The resulting mixture is formed into very small droplets by exposing the mixture to ultrasonic acoustic energy, and subsequently solidifying the droplets to form microbeads.

Substantially all of the microbeads formed by this method have diameters less than about 50 microns. In particularly suitable embodiments, the droplets form microbeads wherein at least 90% (more preferably 99%) of the total number of microbeads formed are less than 50 microns in diameter. The pore size of the matrix is sufficiently small (for example range 1–100 microns) that many of the microbeads are physically entrapped in the matrix. The microbeads may be covalently immobilized in the foam matrix by polymerizing the matrix in the presence of the microbeads that are evenly distributed throughout the polymerizing mass. Covalent immobilization of the microbeads in the matrix has been found especially useful in the present invention because the small size of the beads makes them difficult to maintain in the reactor without loss during process liquid outflow.

In particularly preferred embodiments, the compressible resilient matrix is made of an absorbent foam such as polyurethane, polyvinyl chloride, or polyvinylformal porous membranes. These foams, particularly polyurethane, have been found to efficiently adsorb many pollutants, such as pentachlorophenol (PCP), nitrophenols and many other organic and inorganic pollutants. The adsorptive capacity and rate of adsorption have unexpectedly been found to be increased in the present invention by periodically compressing the matrix. Such periodic compression brings adsorbates into more intimate contact with the matrix, and produces non-laminar flow in the reactor that helps remove the boundary layer from the surface of the adsorptive material. Adsorption in the foam matrix can be further increased by including an adsorptive material such as activated charcoal, chelating agents or biosorbents in the foam matrix, either by addition of the adsorptive material to the foam during or after polymerization or in beads immobilized in the polymerized matrix. Porphyrins, chelating agents, oligonucleotides or biosorbents may also be immobilized in the matrix.

In a particular embodiment of the method, the foam matrix is in a first reactor, and a separate sample of liquid is in a separate reservoir. Compressing the matrix expels at least 10% of the liquid out of the matrix, while subsequent expansion of the matrix draws replacement liquid out of the separate reservoir into the reactor matrix. In particularly preferred embodiments, at least 50% or 75% of the liquid in the matrix is expelled during compression, and in some embodiments at least 90% of the liquid in the matrix is expelled. Such high mass transfer, especially with non-laminar flow, very effectively moves microbial products and wastes out of the matrix, and allows fresh reactants or adsorbates to move into and throughout the matrix. This is a particularly important property if the reactor is being used to perform a sequential biochemical reaction in series with other reactors, or if the reactor is being used as an adsorbent reactor to maximize loading capacity. In some sequential adsorption reactors the pulse frequency could also be low so each matrix would reach equilibrium before compression and expulsion of the liquid to the next matrix where significantly lower equilibrium could be reached. The unidirectional process flow into and through the reactor matrix is also advantageous when performing sequential reactions in a series of such reactors.

The reactor of the present invention is quite versatile, and can be used across a broad range of matrix pulsation frequencies. Suitable pulsation frequencies extend, for example, from less than one cycle per hour or more, to a frequency of at least one cycle per second. Very low pulsation frequencies are preferred when prolonged biological reactions to completion are occurring in the matrix, for example anaerobic degradation with electron acceptors that do not have gas as a product (for example iron or nitrate reduction). Low pulsation frequencies would also be appropriate in synthesis reactions where gases are not formed and high product concentrations are preferred. Very low pulsation frequencies would also be appropriate in sequential adsorption reactors where the pulse frequency could be low so each matrix would reach equilibrium before compression and expulsion of the liquid to the next matrix where significantly lower equilibrium could be reached. Much higher pulsation frequencies are allowed for simple adsorption, for example adsorption of PCP in polyurethane foam. The flexibility of pulsation frequencies allows very good optimization of the reactor kinetics by either increasing or decreasing the pulsation frequency or changing the dwell time during which the matrix is collapsed or expanded.

The microorganisms, enzymes, adsorbents or other active or reactive materials may be suspended throughout the matrix itself by in situ co-polymerization, for example by polymerizing the matrix in the presence of the biological cell or enzymes. Many enzymes have been found to be covalently bound to polyurethane foam because the amines, hydroxyl and carboxyl groups of the enzymes react with isocyanates in the polymerizing polyurethane to form covalent bonds with the polymeric matrix. The biological activity of enzymes and biological cells is better preserved, however, by immobilization in microbeads instead of copolymerization with the matrix.

An important advantage of the present method is that compression of the resilient matrix allows expulsion of liquid from deep within the interior of the matrix. This differs significantly from previous flow reactors in which liquid is moved through biosupports only by the superimposed flow of liquid through the reactor. Liquid that exits a simple flow reactor has physicochemical properties (such as pH, reactant and product concentration) that only poorly approximate the physicochemical conditions in the biomass itself. Compression of the biomatrix of the present invention, however, can immediately transfer liquid mass from the interior of the matrix and from the interior of the beads to a sampling station where physicochemical properties of the liquid from throughout the matrix, including deep within the matrix, can be measured. The pH, substrate, product, process flow velocity, carbon substrate concentration and other process parameters can be altered more accurately to increase the efficiency of a desired reaction deep within the matrix. Moreover, parameters such as pH or substrate concentration may be quickly changed in the matrix because the expanding matrix rapidly draws new process liquid into it and distributes the solution throughout the matrix.

Yet another advantage of the present process is the ability of the reactor to transport liquid through the matrix without requiring external pumping. Compression and expansion of the matrix can instead move liquid into and out of the reactor. Hence one embodiment of the method has a separate reservoir and reactor. Compressing the matrix expels liquid from the matrix and out of the reactor, while subsequent cyclic expansion of the matrix can draw liquid back into the matrix by the sponge-like suction action of the expanding matrix or the chamber that holds the matrix. The reactor can be free floating in a treatment reservoir, and periodically compressed and expanded to exchange liquid between the matrix and reservoir. In such an embodiment, it is preferable that the period between compression and expansion be sufficient (for example one minute, or at least two times longer than the compression time) to allow expelled liquid to move away from the reactor and not be drawn immediately back into the matrix during a subsequent expansion.

In yet another embodiment, the reservoir is a separate container from the reactor, and liquid is expelled out of the reactor during matrix compression. Subsequent expansion of the matrix creates sufficient suction force in the reactor to draw liquid into the reactor from the reservoir through a reactor inlet line, without an auxiliary pump to move liquid from the reservoir into the reactor. In some embodiments, liquid expelled from the reactor by matrix compression then cycles to the reservoir for subsequent return to the matrix in subsequent cycles.

The reservoir preferably has separate inlets and outlets. Liquid that is returned to the reservoir through the inlet preferably is substantially free of liquid that was expelled from the matrix during an immediately preceding matrix compression. The liquid must travel a sufficient distance from the inlet to the outlet that liquid from the inlet does not reach the reservoir outlet in time to be drawn into the matrix on the immediately succeeding matrix expansion. The delay between matrix compression and subsequent expansion should also be short enough (for example less than one second in some cases) that liquid introduced into the reservoir from the reactor does not have time to travel to the reservoir outlet before matrix expansion begins.

In yet other embodiments of the method, the reactor has an upstream inlet and a downstream outlet. The matrix is compressed by a solid piston member that periodically moves in a downstream direction to reduce the volume of the matrix and compress it. Matrix compression moves liquid out of the matrix in a downstream direction without moving liquid out of the matrix in an upstream direction. The matrix is subsequently expanded to draw only upstream process liquid into the matrix. In other preferred embodiments, compressing the matrix expels a reaction liquid from the matrix in a downstream direction through a downstream face of the matrix, while expanding the matrix draws liquid into the matrix in the same direction but through an upstream face of the matrix without drawing liquid in through the downstream face.

Several embodiments of reactors that perform some methods of the present invention are shown in the accompanying detailed description, which proceeds with reference to the following drawings.

BRIEF DESCRIPTION OF THE DRAWINGS

FIG. 3 is a graph comparing polychlorophenol (PCP) adsorption in a polyurethane matrix by a pressure cycled reactor of the present invention (lower curve) and polyurethane foam without pressure cycling (upper curve).

FIG. 4 is a schematic diagram of a syringe pump embodiment of the compressible matrix dynamic bed reactor of the present invention, showing the matrix in an expanded state (FIG. 4A) and a compressed state (FIG. 4B).

FIGS. 7A and 7B are schematic cross sectional views of a fluid piston embodiment of the reactor.

FIGS. 8A, 8B and 8C are alternative embodiments of the reactor shown in FIG. 7, portions of an outer reactor wall being broken away in FIG. 8A.

FIGS. 9A, 9B and 9C are cross-sectional schematic views of another embodiment of the reactor portions of an outer reactor showing movement of a plunger wall to sequentially compress alternating matrices.

FIGS. 10A and 10B are schematic cross-sectional views of two bellows embodiments of the reactor.

DETAILED DESCRIPTION OF SEVERAL PREFERRED EMBODIMENTS

Figure 1:
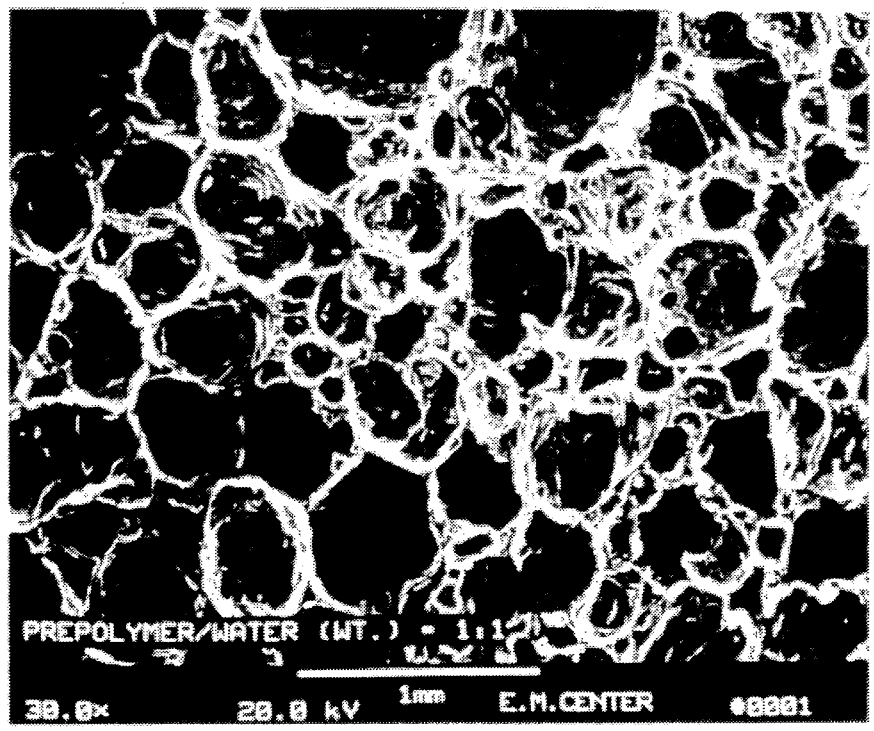
FIGS. 1 and 2 are scanning electron micrographs of a polyurethane matrix with enzymes covalently attached, as shown by gold staining.

The present invention uses a dynamic bed reactor in which a resilient open cell foam matrix is periodically compressed to expel liquid depleted in reactants or adsorbates out of the matrix. Subsequent expansion of the matrix draws fresh process liquid deep into the matrix where microbial, enzymatic, chelating or adsorptive action occurs. Several preferred embodiments of such a reactor are shown in the drawings and described in this specification. Particularly preferred matrix materials are also discussed, as are methods of immobilizing bioactive, enzymatic and adsorptive agents in the matrix. A new method of making very small microbeads for immobilization in the matrix is also disclosed. Finally, data is presented demonstrating the superiority of the present invention to prior reactors.

Compressible Matrix

The compressible matrix of the dynamic bed reactor is preferably a flexible open cell foam material such as polyvinyl chloride, polyurethane, polyvinyl formal, and rubber latex. These and other flexible open cell polymeric foam materials are described in Meinicke and Clark, Mechanical Properties of Polymeric Foams, University of Akron, Akron, Ohio (1973) on page 60. A preferred polymeric foam in the present invention is flexible open cell polyurethane because this material has been found to adsorb and immobilize certain pollutants such as PCP, nitrophenols and other organic and inorganic compounds. The adsorptive capacity of the polyurethane has been found to be further potentiated by its use in the dynamic reactor of the present invention.

Polyurethane also has the advantage of being biocompatible, and capable of providing an immobilization matrix for bacteria such as Flavobacterium that degrade PCP and other pollutants. Biocompatibility of the matrix refers to the ability of the matrix to support a viable culture of organisms without substantially adversely affecting any desired characteristics of the immobilized organisms. In the case of Flavobacterium or tissue culture, the matrix must not reduce the degradation of PCP or growth of the tissue culture. A polymerizable matrix is ideally capable of polymerizing in the presence of the organism or other bioactive material to immobilize the bioactive material without adversely affecting the survival of the cells.

Polyurethanes are a class of polymers synthesized by a reaction between compounds containing an isocyanate group (R—N=C=O) and compounds containing hydroxyl, amine or carboxyl groups. Polyurethanes have previously been shown to be an immobilization matrix for enzymes, organelles and microbial cells. The use of polyurethane immobilized microorganisms for the degradation of aromatic compounds has been shown in U.S. Pat. No. 4,634,672, which is incorporated by reference. Other methods using polyurethane or other matrix immobilized microorganisms or enzymes in biosynthetic or biodegradative reactions are shown in the following papers, which are incorporated herein by reference: Pras, et al. "Kinetic Aspects of the Bioconversion of L-Tyrosine into L-DOPA by Cells of *Mucuna pruriens* L. Entrapped in Different Matrices," *Biotechnology and Engineering* 34:214–222 (1989); Tramper and de Man, "Characterization of *Nitrobacter agilis* immobilized in calcium alginate," *Enzyme Microb. Technol.* 8:472–476 (August 1986); Yang and Su, "Synthesis of Aspartame Precursor: α-L-Aspartyl-L-Phenylalanine Methyl Ester in Ethyl Acetate Using Thermolysin Entrapped in Polyurethane," *Biotechnology and Bioengineering* 32:595–603 (1988); Lorenz et al., "Immobilization of Yeast Cells in Polyurethane Ionomers," *Biotechnology and Bioengineering* 29:388–391 (1987); Dominguez et al., "Carbodiimide coupling of β-galactosidase from *Aspergillus oryzae* to alginate," *Enzyme Microb. Technol.* 10:606–610 (October 1988); Lawton et al., "Immobilization of Whole Cells Using Polymeric Coatings," *Biotechnology and Bioengineering Symp.* No. 17:507–517 (1986); McGhee et al., "Continuous Bioconversion of Starch to Ethanol by Calcium-Alginate Immobilized Enzymes and Yeasts," *Cereal Chemistry* 61(5):446–449 (1984); Chakrabarti and Storey, "Co-immobilization of amyloglucosidase and pullulanase for enhanced starch hydrolysis, 38 *Appl. Microbiol. Biotechnol.* 33:48–50 (1990); Grootjen et al., "Fermentation of glucose and xylose with immobilized *Pichia stipitis* and *Sacchromyces cerevisiae,*" *Enzyme Microb. Technol.* 12:860–864 (November 1990); and Miyazaki and Croteau, "Immobilization of cyclase enzymes for the production of monoterpenes and sesquiterpenes," *Enzyme Microb. Technol.* 12:841–845 (November 1990). These incorporated papers illustrate a variety of biochemical reactions that can be performed in a polyurethane matrix, such as that of the present invention.

W. R Grace and Company, which manufactures many polyurethanes and polyurethane prepolymers, has published numerous methods by which the in situ polymerization of medium chain molecular weight chains is exploited for biocatalyst entrapment. Rosevear et al., *Immobilized Enzymes and Cells,* Adam Hilger, Philadelphia, Pa., p. 71. In the work described in Example I below, polyurethane foam (PUF) was made from prepolymer HYPOL FHP 2000 or 3000 (W. R Grace and Company), as described in O'Reilly and Crawford, "Degradation of pentachlorophenol by polyurethane immobilized Flavobacterium cells,." *Appl Environ Microbiol* 55(9):2113–2118 (1989), which is incorporated by reference herein.

EXAMPLE I

Immobilization of polychlorophenol (PCP) in a polyurethane foam (PUF) matrix is described in this example, and data is presented to show enhanced adsorption of PCP into the matrix in a dynamic bed reactor.

Figure 5:
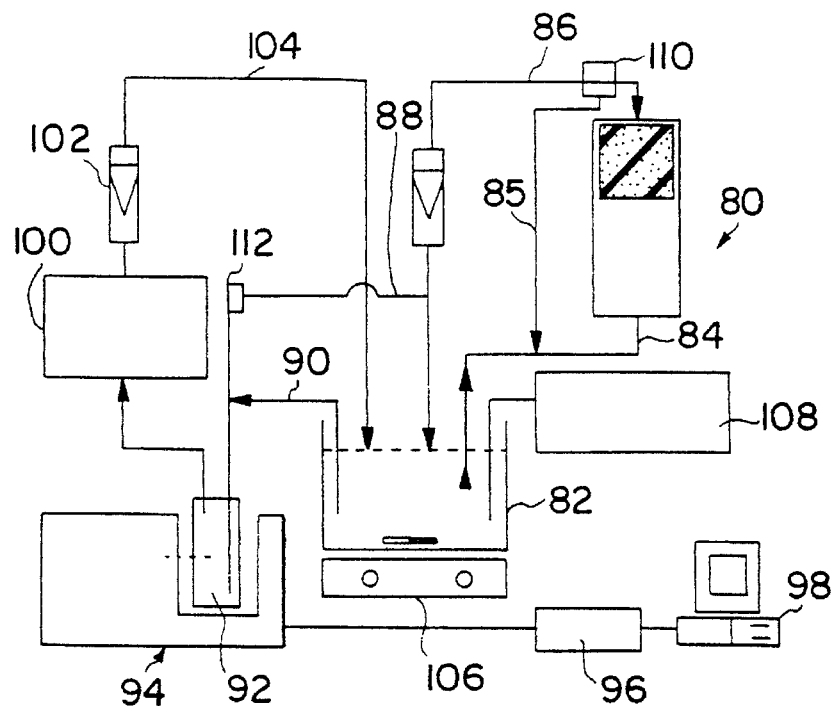
FIG. 5 is a schematic diagram of another dynamic bed reactor of the present invention for monitoring a physicochemical property of liquid expelled from the dynamic bed reactor, and monitoring the progress of a reaction in the reactor.

The properties of PUF immobilized enzyme were characterized by using a dynamic bed reactor recirculation system shown in FIGS. 4–6.

A dynamic bed reactor (DBR) was constructed as shown schematically in FIG. 4 to include a reservoir 20, a syringe pump 22, an upstream liquid inlet line 24 between reservoir 20 and syringe pump 22, and a downstream flow line 26 that returns from pump 22 to reservoir 20. An oxygen bubble introduction member 28 extends into the bottom of reservoir 20 to oxygenate a liquid 30 in the reservoir.

The syringe pump 22 includes a cylinder 32 and piston 34 that reciprocates in the cylinder from a retracted position shown in FIG. 4A to an extended position shown in FIG. 4B. The piston 34 has a flat solid piston face 36 that forms an annular seal with the interior wall of cylinder 32. The volume of cylinder 32 between flat face 36 and distal end 38 is a pump chamber in which is located a polyurethane matrix 40. No microorganisms, enzymes, chelating agents, or bioactive material is immobilized in this matrix for this example. The dimensions of the matrix in this example were sufficient to fit the dimensions of a 10 cc syringe barrel. A 1.5 cm diameter by 6 cm long matrix was used, but much larger dimensions such as 3 cm by 10 cm could be compressed and would also be quite suitable in this 10 cc syringe barrel. This precompression allows more adsorptive or biological density than in other foam immobilized reactors. Much larger syringes are available and would be used on a larger scale. A single large matrix can be used, or multiple small pieces of polyurethane can be compressed together to effectively provide a single matrix that substantially fills the pump chamber, particularly during matrix compression. Channeling is avoided with multiple and single pieces of foam due to the actual compression and expansion of the foam as an effective unit, and the resulting absence of non-laminar flow in the pump chamber.

Figures 6A, 6B:
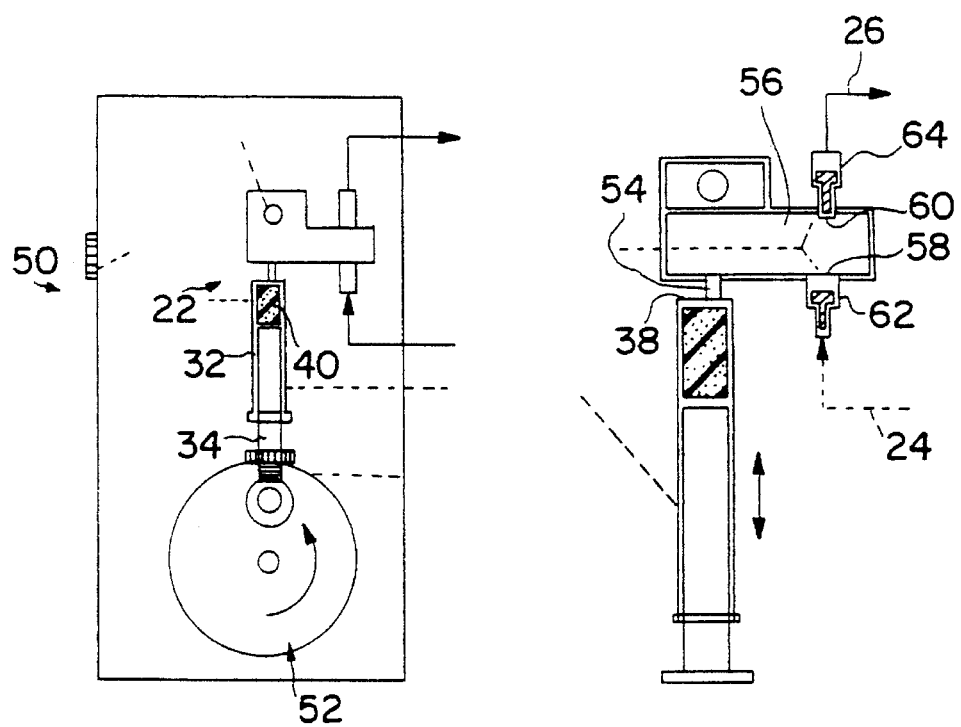
FIGS. 6A and 6B are enlarged, somewhat schematic views of the syringe pump of FIG. 4.

An enlarged view of the piston pump is shown in FIG. 6 to include a reciprocating variable speed miniPump 50 from Laboratory Data Control, a Division of Milton Roy Company, Chicago, Ill. The miniPump was modified so it could operate at the cycle and dwell times stated in this Example. The miniPump has a rotating cam 52 that periodically advances and retracts piston 34 to compress and expand matrix 40. Advancing piston 34 reduces the volume of the pump chamber and compresses matrix 40. As seen best in FIG. 6B, a liquid passageway 54 extends from an opening in the distal end face 38 of cylinder 32 to a chamber 56. The chamber 56 has an inlet 58 and an outlet 60, with a one way valve 62 in inlet 58 that allows flow only into the chamber, and a one way valve 64 in outlet 60 that allows liquid only out of the chamber. A pivot mounting allows chamber 56 to pivot in response to oscillations of cam 52. Silicon tubing is attached to inlet 62 to form inlet line 24, and to outlet 60 to form outlet line 26.

Referring to FIGS. 4 and 6, the syringe was fed from reservoir 20 containing 100 ml of 100 ppm PCP in pH 7.3, 50 mM HEPES buffer at 25° C. The foam used had a porosity (volume of water held by foam/total volume of soaked foam) of 0.89. Using a cycle time of 2 seconds and a 50% compression, PCP adsorption in the polyurethane foam was determined by measuring the concentration of PCP in the reservoir and the results are shown (□) in FIG. 3. FIG. 3 also shows PCP adsorption in polyurethane foam that is not subject to pressure cycling with periodic foam compression (x). That data was obtained by spectrophotometric measurements at 320 nm of 1 ml samples removed from the stirred reservoir 20 and then returned following measurement. Similar masses and sizes of polyurethane foams were placed in either the well-stirred reservoir 20 or in the pump chamber 32. Tests were run with both reactors side by side using pieces of foam from the same original blocks of polyurethane and repeated. The concentration of PCP remaining in solution in the liquid was plotted vs time in FIG. 3.

FIG. 3 shows that the DBR adsorption was superior to non-DBR adsorption. The concentration of free PCP decreased more quickly in the liquid cycling through the DBR (bottom curve), and plateaued at a lower concentration of free PCP. These results indicate that adsorption of PCP in PUF is enhanced by the dynamic bed reactor in which the foam matrix is periodically compressed. These results were obtained in the absence of any supplemental bioactive or chelating agent, and reflect the enhanced adsorptive capacity of the PUF itself.

EXAMPLE II

Beta-D-galactosidase was successfully immobilized in PUF in this example, and scanning electron microscopy (SEM) with energy dispersion X-ray (EDX) microanalysis, combined with immuno-gold labeling techniques, was used to investigate the immobilization mechanism of the enzyme in PUF.

A syringe pump 80 (FIG. 5), which was similar to syringe pump 22, is described in this example and later used in Example IV to monitor enzymatic degradation of o-nitrophenyl galactosidase (ONPG) by matrix immobilized beta-galactosidase. ONPG was made into a 10,000 ppm stock solution in 0.25M NaOH, and 313 ml of the base stock was placed in a 125 ml flask that acted as a reservoir. Tubing formed an inlet line 84 into syringe pump 80, and an outlet line 86 out of pump 80. Inlet line 84 brought liquid only from reservoir 82 through a one way valve to pump 80, while outlet line 86 moved fluid only out of pump 80 through a one-way valve to reservoir 82. Although not used in this example, an additional line 88 could be provided with the capability to allow liquid from outlet line 86 to be directed thorough valve 112 into flow cell 92 to be analyzed before dilution in the reservoir. This would allow process control for optimization of reactor efficiency by adjusting cycle parameters.

A flow line 90 from reservoir 82 leads to a flow cell in a SPECTRONIC 1001 spectrophotometer 94 attached to an integrated circuit board 96 and an IBM-PC Computer 98. Liquid from flow cell 92 moves through a reciprocating miniPump 100, a flow meter 102, and line 104 back into reservoir 82. A magnetic stirrer 106 under reservoir flask 82 stirred liquid in the reservoir during this example. A pH controller 108 monitored and controlled pH in the reservoir 82. Although not used in this example, a separate pH controller 110 may monitor the pH of liquid immediately as it comes out of pump 80 into outlet line 86, and control the pH as it enters pump 80 through line 84. In large systems it is not feasible or desired to adjust pH or add nutrients, etc. to the entire reservoir before the liquid enters the reactor 80 from reservoir 82. By monitoring the physicochemical property, such as pH of the liquid moving through outlet 86, the controller can inject into the inlet 84 (for example through a line 85) controlled amounts of an acid or a base for pH adjustment. The pH controlling substances introduced into inlet line 84 will then be well mixed by the non-laminar flow as the liquid enters the reactor 80. Monitoring in the outlet line 86 will give feedback to properly determine the correct amount of acid, base, etc to inject into inlet line 80 during an immediately following expansion of the matrix.

The automatic pH controller with pump module is commercially available from New Brunswick Scientific Co., Inc., in Edison, N.J.; a flow-through quartz cuvette was made in the laboratory; and an ultraviolet/visible spectrophotometer (Spectronic 1001) from Bausch & Lomb, Inc., Rochester, N.Y. was used. For the preparation of PUF from prepolymers a 50 ml smooth flat bottom glass tube with pressure and temperature control was used as a polymerization reactor. The pH measurements were made with a Fisher Model 825 MP digital pH/millivolts meter.

Polyurethane prepolymers (HYPOL FHP2000 and 3000) were supplied by W. R. Grace Co., Lexington, Mass., and stored in a desiccator. Polyurethane foam was made by the reaction of prepolymer with water or with enzyme stock solutions. Surfactant (Tween 80) and 25° glutaraldehyde aqueous solution were from Aldrich Chemical Co., Inc., Milwaukee, Wis. Bicinchoninic Acid (BCA) protein assay reagent was purchased from Pierce Chemical Company, Rockford, Ill., colloidal gold solution (0.01°/o gold chloride, 40 nm) from BioCell Research Laboratory, and filter paper (0.45 mm) from Millipore, USA. The chemicals for preparing citrate-phosphate, phosphate, and Tns-HCl buffers, o-nitrophenyl beta-D-galactoside, o-nitrophenol and all other general chemicals were bought from Sigma Chemical Company, St. Louis, Mo. The beta-D-galactosidase was also obtained from Sigma (E3.2.1.23, Grade XI, from Aspergillus oryzae).

The dynamic bed reactor and reservoir were water jacketed to maintain constant temperature. The reaction solution in the reservoir was fully mixed by the magnetic stirrer and was pumped through the flow cell by the reciprocating miniPump. Teflon tubes were required for the connections between the flow cell and the reactor system to avoid the adsorption of chemicals analyzed. Sliced round cylinders (5 mm thick; 22 mm diameter) of foam were packed in the syringe tube as the reactor bed. In operation, the bed was compressed by the piston then released by the elasticity of foam itself, thus operating dynamically. The output electrical signal (in volts V) of the spectrophotometer was transmitted through an integrated circuit board (DASH-8) to the computer (IBM-PC AT) where ONPG concentration versus time curves were computed, displayed, and stored.

Bicinchoninic acid (BCA) reagent was used for the assay of proteins for both soluble and immobilized enzymes. Copper II ions in the working reagent are reduced to copper I ions in the presence of protein in an alkaline medium (biuret reaction). The copper I ions then chelate with two BCA molecules to give a water soluble purple product. The higher the protein concentration, the deeper the purple color.

The BCA protein assay working reagent was prepared by mixing fifty parts of reagent A and one part of reagent B (Pierce product instructions, booklet 23225). This working reagent is stable for at least one week at room temperature. Solutions of purified bovine serum albumin (BSA) in 0.9% sodium chloride and 0.05% sodium azide were used to make a standard protein assay curve. This enhanced protocol was chosen because of its higher sensitivity and color stability. Samples (0.1 ml) and working reagent (2 ml) were pipetted into sterilized vials with caps, mixed well, and then incubated in a heat block held at 60° C. for 30 minutes. After incubation all samples were cooled to room temperature. A spectrophotometer (Spectronic 2000, Bausch & Lomb) with autosampler was used to measure the absorbance at 562 nm.

This example was performed with the enzyme (beta-D-galactosidase) immobilized in the polyurethane matrix. Enzyme immobilization was achieved by in situ co-polymerization. The high purity one-component foamable hydrophilic polyether polyisocyanate prepolymers (HYPOL FHP 3000, 2000 and 2002 from W. R. Grace) were derived from toluene diisocyanate (TDI) and have the ability to react with prootic (active hydrogen containing) compounds and form elastomeric foam products. The HYPOL 3000 and 2000 contain, respectively, less than 10 and 5 percent by weight of free TDI. This low level of TDI improves the biocompatibility of the matrix, particularly when using the matrix as a support for immobilized biocatalysts as in this example.

To prepare PUF-immobilized enzyme, 1 g of HYPOL 3000 prepolymer was weighed and 1 ml cold enzyme stock solution (beta-galactosidase 5 mg/ml in Ph 7.3 phosphate buffer) was added to the 50 ml tube reactor cooled by a ice-water bath. The mixture was stirred vigorously to achieve a homogeneous distribution of enzyme within the prepolymer. Mixing time was less than 20 seconds during which time extensive polymerization was detected visually. The resulting foams were allowed to cure at room temperature (20° C.) for at least 30 minutes. After polymerization was complete, a foam cylinder with a 22 mm diameter was cut into round slices with 5 mm thickness, and then washed and squeezed continuously in the DBR by water (1 to 5 liter). The enzyme leakage was monitored by the BCA protein assay. The amount of immobilized enzyme was calculated by a material balance. The foam slices with immobilized enzyme were stored in buffer phosphate, pH 7.3 at −20° C.

EXAMPLE III

The PUF structure made in Example II was examined by scanning electron microscope (SEM, Amray, Model 1830). The physical properties of the PUF, such as density, free volume fraction (or porosity) were determined based on the weight measurement of wet and dry foams.

Figure 2:
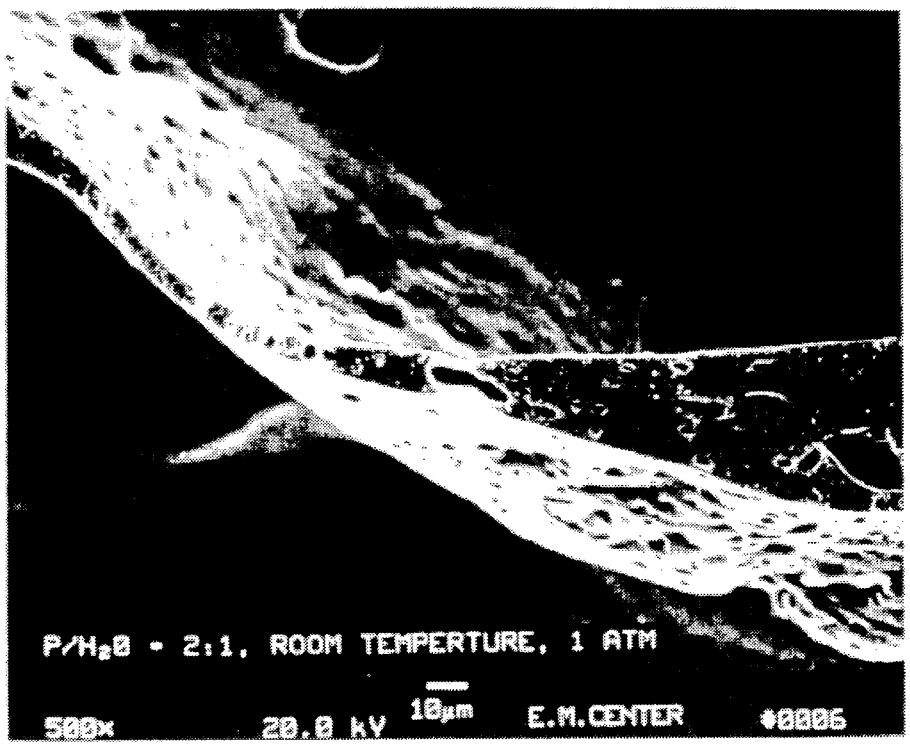

SEM-EDX microanalysis of gold-labelled enzyme in PUF was accomplished with immunogold labelling. Enzyme molecules were first strongly adsorbed to gold particles by electrostatic interactions between the negatively charged surface of gold particles and positively charged groups of the protein. The enzyme-gold conjugates were then immobilized in the PUF as described before. Samples of approximately 1 mm slices coated with carbon powder were prepared. SEM (Amray, Model 1830) and energy dispersion x-ray (EDX, Noran, Model 5500) microanalysis was used for locating the labeled immobilized enzyme and analyzing its surface density. An enzyme gold complex was formed, and the enzyme-gold complex was suspended in 2 ml of 0.01M pH 7.3 sodium phosphate buffer. One mL of this buffered gold probe solution was used for immobilization in PUF. The SEM pictures of HYPOL FHP3000 flexible foams prepared under typical conditions of enzyme immobilization are shown in FIGS. 1 and 2. It can be seen that the PUF porous open-cell structure consists of macropores (or bubbles) separated by thin membranes (or strands). Since bubble volume fraction is greater than 76%, the bubbles are quasi-spherical membrane cells. There is at least one window between macropores on each membrane. The membranes are also porous on the micro scale view and there are many separate micropores within the membrane. The macropore size is approximately 0.5 mm or 50 ppi (pores per linear inch); membrane thickness varies from 5 to 50 μm; windows are about 10 μm; and micropore size varies from 0.1 to 20 μm. The apparent density is 0.15 g/cm$^3$ for dry or 1.05 g/cm$^3$ for wet PUF, which is in the medium foam range (0.1 to 0.4 g/cm$^3$); the porosity is 89%; the swelling factor (wet diameter/dry diameter of cylinder) is 1.294.

The SEM-EDX analyses of PUF immobilized enzyme samples clearly showed white dots representing surface locations of immobilized enzymes labelled by gold particles. The surface density of labelled enzyme was uniform and approximately 25 dots per 1000 $\mu m^2$. For the unloaded (enzyme-free) PUF, no white dots were observed. The immobilized enzyme preparation was strongly washed by deionized water after the immobilization. Then the same immobilized enzyme was cut into two slices, and the cutting surface of one of them was strongly washed again while the other was not. The washed SEM sample contained about 70% of the gold elements of the unwashed SEM sample, indicating that 70%, of the immobilized enzymes were strongly fixed to PUF by forming water insoluble enzyme-polymer conjugates via covalent bonds and thus could not be washed off. Approximately 30% of the immobilized enzymes may be entrapped in micropores of PUF.

EXAMPLE IV o-Nitrophenol (ONP) was produced during the hydrolysis of ONPG by beta-D-galactosidase in the reactor system of Example II (FIG. 5). The liberated o-nitrophenol was analyzed spectrophotometrically at its absorbance maximum of 420 nm for basic and 350 nm for acidic solutions. The standard activity of beta-D-galactosidase used for all the experiments, unless stated otherwise, was 5.6 U/mg solid enzyme powder (where 1 U is defined as the amount of enzyme that hydrolyzes 1.0 micromole of ONPG per minute at pH 4.5 and 30° C. The standard buffer used for all enzyme experiments was 0.1M phosphate, pH 7.3.

The superior adsorption characteristics of the dynamic bed reactor were illustrated in a series of comparative experiments in which batch reactions were carried out as follows. For free enzyme activity measurement, 1 mL enzyme stock solution was added to 50 mL buffered (pH 7.3) substrate solutions in a 125 mL stirred reservoir placed in a water bath at 37° C. For immobilized enzyme measurement, l/g (dry) PUF (diameter 22 mm and thickness 5 mm discs) biocatalyst matrix was packed in the syringe tube and 50 mL buffered (pH 7.3) substrate solution were added to the reservoir at 37° C. and pH controlled by an automatic pH controller. The average flow rate through the DBR was 150 ml/min with piston cycle time about 1 second and 50 percent compression ratio of the dynamic bed. Initial rates from the linear section of kinetic curves were used for determination of the activity (AU/min.g dry immobilized biocatalyst preparation).

The activities of free and immobilized beta-galactosidases were determined using 0.1M HCl-NaCl buffer (pH 2.2), 0.1M titrate-phosphate buffer (pH 2.6 to 7.0), 0.1M phosphate buffer (pH 7.3) and 0.1M Tris-HCl buffer (pH 8.5).

Figure 14:
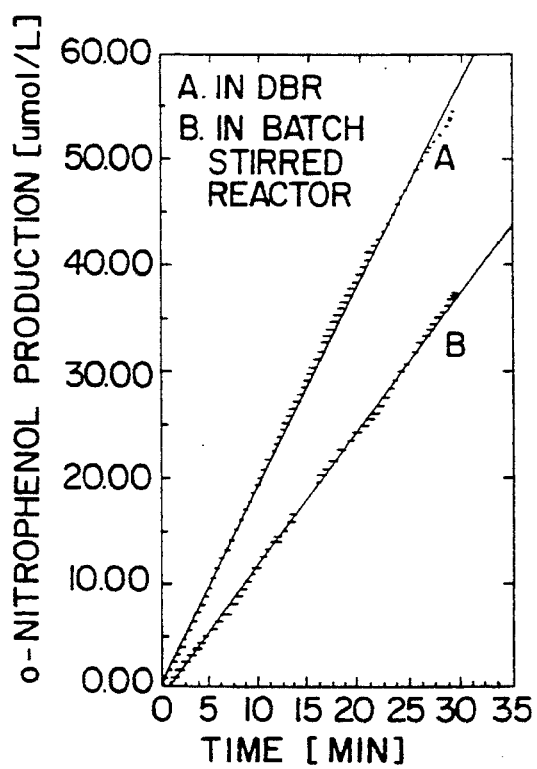
FIG. 14 is a graph comparing initial hydrolysis rates of ONPG to ONP in the presence of polyurethane foam immobilized beta-galactosidase enzyme in a dynamic bed reactor (A) and a batch stirred reactor (B).

Initial experiments were carried out to determine the extent of external and internal substrate diffusional limitations. When the PUF immobilized enzyme was placed in the reservoir 82 and stirred, the external mass transfer resistance was easily avoided at high stirring speeds. All the later activity measurements were carried out under this agitation condition. Internal mass transfer was not eliminated unless the PUF immobilized enzyme was operated in the DBR. FIG. 14 shows a comparison of hydrolysis of ONPG to ONP by the PUF immobilized betagalactosidase (1 g dry foam slices with 22 mm diameter and 5 mm thickness) operated in a batch stirred reactor (line B) and a DBR (line A). The concentration of ONP increased much more quickly in the DBR, as shown by the greater slope of the DBR line, indicating a faster enzymatic reaction rate.

Figure 15:
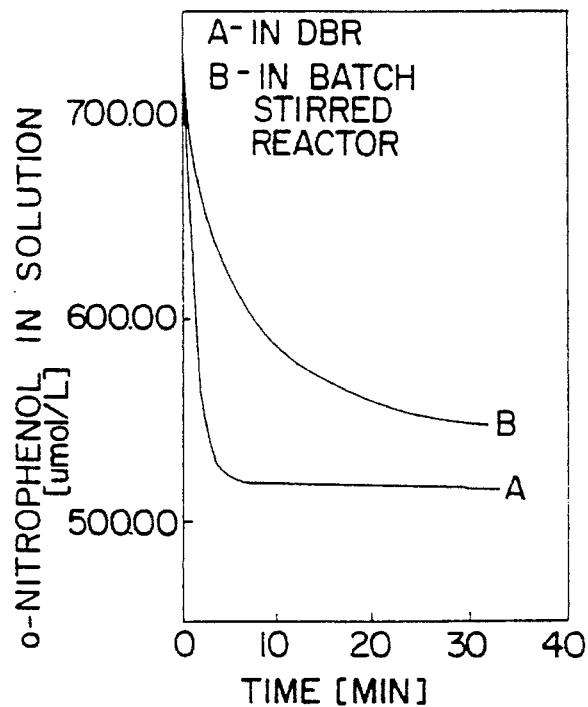
FIG. 15 is a graph comparing adsorption of ONP to polyurethane in a dynamic bed reactor (A) and a batch stirred reactor (B).

The o-Nitrophenol was observed to adsorb to the PUF matrix, as shown in FIG. 15. To produce this data, six slices of enzyme free PUF (1 g 80° C. oven dried) were used to adsorb o-nitrophenol. Adsorption occurred in a 50 ml beaker with stirred 100 ppm o-nitrophenol in pH 7.3 sodium phosphate buffer at 37° C. Concentration of ONP in the reactor solution was measured for 30 minutes, and the results plotted in FIG. 15 as curve B. For comparison, a 1000 ppm solution of the ONP was passed through the enzyme free PUF of the dynamic bed reactor 80, the concentration of ONP in beaker 82 measured over a similar period of time, and the results plotted on curve A in FIG. 15. This graph shows that passing the ONP through the dynamic bed reactor (curve A) much more rapidly adsorbs the ONP into the PUF than merely stirring pieces of foam in a beaker with ONP (curve B). Adsorption of ONP is also greater with a DBR, as evidenced by lower concentrations of ONP in the DBR reservoir as compared to the stirred beaker at steady state after 30 minutes.

EXAMPLE V

Figure 16:
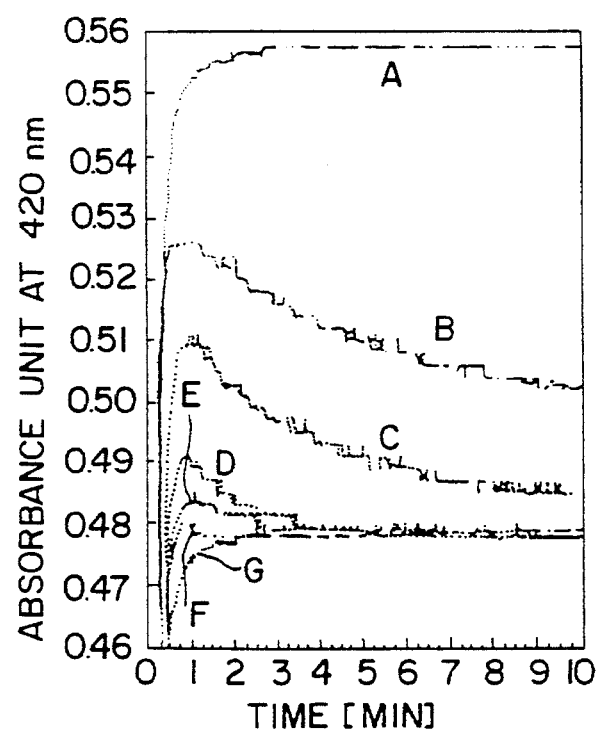
FIG. 16 is a graph showing ONP concentration in a reservoir over time for curves (from top to bottom) from batch stirring polyurethane foam cubes of decreasing size in a reservoir, using a foam cylinder in a dynamic bed reactor, and powdered polyurethane foam.
Figure 17:
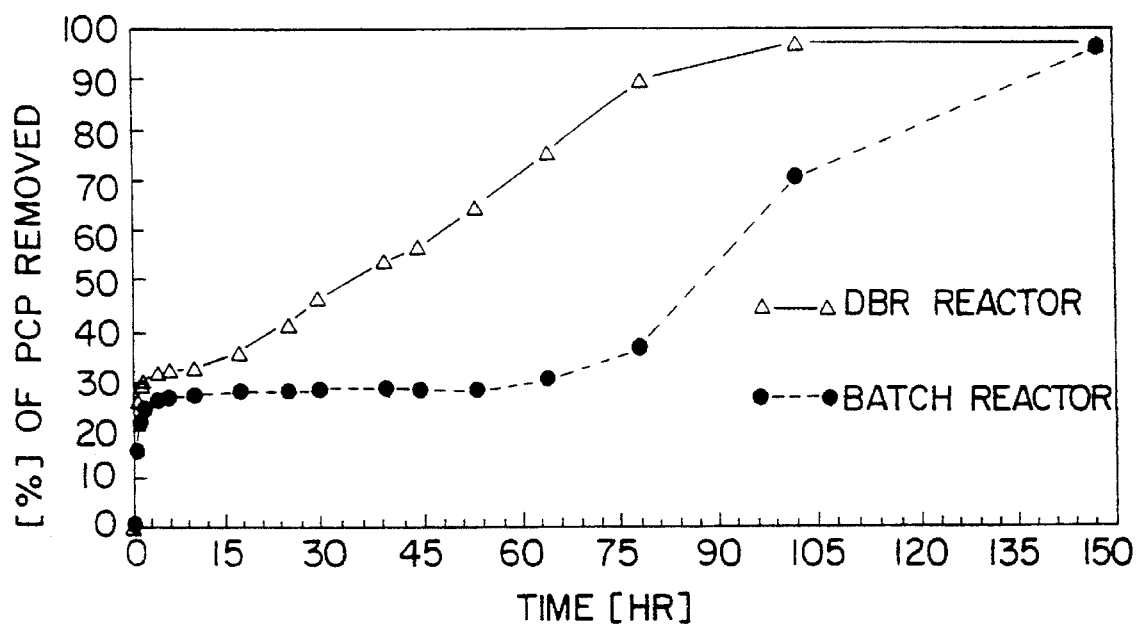
FIGS. 17 and 18 are graphs comparing degradation of PCP by immobilized Flavobacterium in a batch reactor and a dynamic bed reactor.

Under the same weight basis (0.43~dry), different sizes of unloaded foam cubes and ground foam particles were added in the batch stirring reactor, and unloaded (enzyme-free) cylindrical foam was added in the DBR for ONP adsorption tests. In each case, an equal mass of polyurethane foam was added (0.43 g dry weight). A droplet of ONP stock was added to the pH 7.3 phosphate buffer solution to create a pulse signal, and the concentration of the ONP monitored in the spectrophotometer for ten minutes. Curves are shown in FIG. 16 for no foam cubes (A), and foam cubes having the following dimensions: 10 $mm^3$ (B); 5 $mm^3$ (C); 2.5 $mm^3$ (D); and 1 $mm^3$ (E) in the batch stirring reactor. A DBR with a foam cylinder (22 mm diameter by 30 mm length) was used in the DBR, and the concentration of ONP in the beaker over time recorded on curve F. Finally, finely ground foam particles less than 0.1 mm diameter were placed in the beaker, no DBR was used, and the results are shown on curve G. As can be seen by the relative order of the curves in FIG. 16, the DBR much more efficiently adsorbs ONP than foam particles, unless those particles are less than 0.1 mm diameter. As can be seen in FIG. 16, the adsorption rate increases with the decrease of PUF particle sizes.

EXAMPLE VI

Initial enzymatic reaction rates as a function of pH and temperature were determined for the matrix immobilized beta-galactosidase of Example II. For both free and immobilized enzymes, initial rates increased with increasing temperature below 60° C. Enzyme inactivation began at approximately 60° C. The optimum operational temperature for both free and immobilized enzymes was approximately 50° C.

Figure 13:
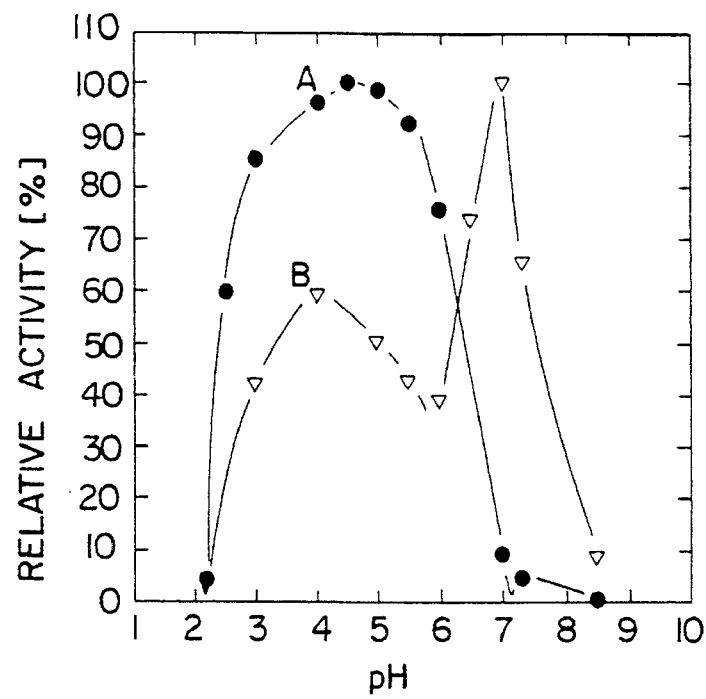
FIG. 13 is a graph showing optimum pH for free and matrix immobilized beta-D-galactosidase.

The pH profiles for both free and PUF immobilized beta-galactosidase are shown in FIG. 13. The optimum pH for free beta-galactosidase was from 4.0 to 5.0. For the immobilized beta-galactosidase, however, the maximum rate was shifted to a higher pH (around pH 7.0) with a second optimum rate around 4.5. As compared with the pH profile for native galactosidase, the PUF-immobilized galactosidase has a broader active range and greater resistance to alkaline conditions. Also, this pH profile with two optimum pH ranges is consistent with the SEM-EDX microanalysis that most of the enzyme is immobilized by covalent bonding and a lesser amount of immobilized enzyme is physically entrapped inside the pockets of PUF. The covalently-bonded enzyme corresponded to the optimum pH around 7.0, while the physically entrapped enzyme still gives an optimum pH around 4.5.

EXAMPLE VII

PUF Immobilization Methods

The physical structure of PUF and the reactivity of urethane prepolymer make enzyme immobilization possible by adsorption, entrapment or binding. Based on the SEM-EDX microanalysis in Example III, the excellent operational stability of the matrix, and the characteristic pH profile of PUF immobilized galactosidase in Example V, it was concluded that the majority of the PUF immobilized enzyme was covalently bound. This conclusion is also justified by considering the foam synthesis mechanism from the prepolymer. In the primary reaction stage of the foaming processes, isocyanates react with different active hydrogen compounds as follows: Aliphatic NH2>aromatic NH2>primary OH>water>secondary OH>tertiary OH>phenolic OH>COOH. When the enzyme solution is mixed with prepolymer, the primary amine groups of enzyme apparently replace some of the amines resulting from the decomposition of carbamic acid (R~HCOOH) in reactions with isocyanate to produce substituted ureas.

In addition to the in-situ copolymerization method, other immobilization methods were attempted. For the case of adsorption of beta-galactosidase with preformed foams, no activity was detected in the matrix after the matrix was washed, indicating that beta-galactosidase is not immobilized by adsorption. A cross-linking agent was also used to enhance the loading capacity of PUF by aggregating enzymes. However, the deactivation of beta-galactosidase was significant in the presence of 1% glutaraldehyde.

Compared to other immobilization methods, in situ copolymerization has numerous advantages. Immobilization procedures are simple and can be performed under mild conditions that do not significantly affect enzyme activity. Prepolymers also do not contain monomers which denature enzymes. Isocyanate groups in the prepolymer react to covalently bind enzymes, and the network structure of PUF matrices can be controlled using prepolymers of different chain lengths or by changing the foaming conditions. Enzymes containing free primary amino groups (NH2) appear to be covalently bound particularly well.

Additional Dynamic Bed Reactor Embodiments

The versatility of the dynamic bed reactor is illustrated in the following examples of alternative embodiments of the design.

FIG. 7 shows an air expansion chamber design in which movement of a flexible imperforate rubber or otherwise elastic diaphragm changes the volume of the matrix. The imperforate nature of the diaphragm 158 does not allow liquid out of matrix 162 into chamber 160. A metal tank 150 has an opening 152 that communicates with an inlet line 154 and an outlet line 156. One way valves (not shown) in the lines 154, 156 allow unidirectional flow only in the directions of the arrows in the inlet and outlet lines. A flexible rubber diaphragm 158 divides the interior of tank 150 into an upper air chamber 160 and a lower foam matrix chamber that is substantially completely filled with a matrix 162 such as a polyurethane foam cylinder. The foam matrix substantially completely fills the matrix chamber when the matrix chamber is fully expanded (FIG. 7A) and fully compressed (FIG. 7B). The polyurethane is preferably precompressed before placement in the matrix chamber so that the fully expanded matrix pushes upwardly to displace diaphragm 158 to the position shown in FIG. 7A.

In operation, air chamber 160 in FIG. 7A is pressurized from a source of pressurized air that is not shown in the drawings. Increased fluid pressure in chamber 160 pushes the diaphragm 158 downwardly into matrix 162 thereby reducing the volume of the foam matrix chamber. Liquid and gas in matrix 162 is exhausted through the one-way valve in line 156. After complete pressurization of chamber 160, the matrix is in the collapsed position shown in FIG. 7B in which substantially all liquid in the matrix has been expelled out of opening 152 and through unidirectional outlet line 156. Air in chamber 160 is then bled out of the tank 150 into an air supply reservoir, exhausted to the atmosphere, or vented into the inlet supply reservoir for later introduction as dissolved gas through line 154. The resilience of matrix 162 then expands the matrix chamber by pushing upwardly against diaphragm 158 until the matrix regains its fully expanded condition shown in FIG. 7A.

Another embodiment is shown in FIG. 8 in which a tank 180 contains a flexible diaphragm 182 that divides the tank into separate, non-communicating matrix chambers respectively filled with a matrix 184 in one chamber and a second matrix 186 in the other chamber. The chamber that contains matrix 184 communicates through a fluid manifold 187 with a fluid conduit line 188. The chamber that contains matrix 186 similarly communicates through a fluid manifold 190 with a fluid conduit line 192. The lines 188, 192 both are connected to a four way switching valve 194, which is shown schematically in FIGS. 8B and 8C. Valve 194 in turn communicates with fluid inlet 196 and fluid outlet 198. Fluid moves through inlet 196 from a reservoir that is under pressure greater than the compression pressure of the matrix, and through outlet 198 to a collection vessel under a lesser pressure than the matrix, or back into the reservoir from which it came.

As seen in FIGS. 8B and 8C, the switching valve moves between a first position (FIG. 8B) and a second position (FIG. 8C). In the first position shown in FIG. 8B, fluid from line 188 moves through valve 194 into outlet line 198 to exhaust fluid from the matrix 184. Fluid from line 196 moves into line 192 to convey fluid into matrix 186. In the second position shown in FIG. 8C, the valve has switched to a position in which fluid from inlet 196 moves into through 188 into matrix 184, while fluid from line 192 moves through outlet 198 to exhaust fluid from matrix 186.

In operation, beginning with the valve in the state shown in FIG. 8C and the reactor in the condition shown in FIG. 8A, fluid has flowed into matrix 184 through inlet 196, line 188 and manifold 187 to fill matrix 184 and displace diaphragm 182 toward matrix 186. As the diaphragm was displaced into matrix 186, the matrix 186 was compressed to exhaust liquid through manifold 190 into line 192, through line 194 and out outlet 198. The valve 194 is then switched to the position shown in FIG. 8B, such that fluid in matrix 184 is allowed to exhaust through manifold 187 to line 188 and outlet 198 as fluid is drawn in through lines 196, 192, manifold 190, into matrix 186. The resilience of expanding matrix 186 as it fills with fluid, together with fluid pressure from inlet 196, provides a force to displace diaphragm 182 toward matrix 184 and squeeze fluid out of and collapse matrix 184.

Subsequently changing the position of valve 194 back to the position shown in FIG. 8C reverses the direction of flow within the system to expel fluid from matrix 186. As can be seen in this embodiment, high efficiency mass transfer to an adsorbent can also occur with fluids other than just a liquid. For example, gas, vapor or mixtures of gases, vapors and liquids can have adsorbate removed inside the matrix. Since the reactor operates under a pressure from inlet 196, cavitation, vapor lock, channeling and poor mixing will not occur. The alternating cycle described in this example continues for a desired number of cycles at rates optimized for the specific reactor or adsorption.

Yet another embodiment of the dynamic bed reactor is shown in FIGS. 9A, 9B and 9C, which is suitable for immersion in a liquid treatment pond or in a floating platform in such a pond. The reactor comprises two precompressed matrices 200, 202 separated by a liquid impermeable solid or imperforate plunger member that reciprocates back and forth between positions shown in FIGS. 9B and 9C. Matrix 200 is frictionally held between plunger 204 and an end plate 206, wherein plate 206 is liquid permeable because of perforations in that plate. Matrix 202 is similarly frictionally engaged between plunger 204 and a perforated end plate 208.

A neutral position of the reactor is shown in FIG. 9A in which the plunger is in a neutral mid-way position. Both of the matrices are firmly frictionally engaged in the reactor because they have been precompressed such that both matrices are partially compressed in FIG. 9A. As plunger 204 moves toward matrix 200 (FIG. 9B), matrix 200 is compressed to expel liquid from it through the perforations in plate 206, and through the open floor or open sides of the reactor. During compression of matrix 200, the matrix 202 is cooperatively allowed to expand and draw process liquid deep into the matrix. Plunger 204 is then moved to the position in FIG. 9C in which matrix 202 is compressed to expel liquid through perforations in plate 208, and draw fresh process liquid into expanding matrix 200. It is preferable to allow sufficient time between compression and expansion of each matrix that liquid expelled from the matrix during a given compression moves away and is not taken into the matrix during an immediately succeeding matrix expansion.

The embodiment of FIG. 9 could be varied by substituting solid walls for the perforated walls of end plates 206, 208. Each matrix could instead be held in a closed compartment with close fitting walls, but the plunger would still be free to move back and forth. One way valves could be placed in the walls of each compartment, and in the plunger wall, so that expansion of matrix 200 would draw into the matrix liquid from outside the compartment but not from the compartment holding matrix 202. Compression of matrix 200 would then move liquid through the one-way valve in plunger wall 204, into the compartment that holds matrix 202 while matrix 202 is expanding as the plunger moves against matrix 200. Subsequent compression of matrix 202 then expels liquid from matrix 202 through one way valves in the compartment that holds matrix 202, and out of the compartment into the surrounding liquid.

A final disclosed embodiment of the dynamic bed reactor is shown in FIGS. 10A and 10B, in which a polyurethane foam matrix 220 substantially fills an interior chamber of a bellows that has top and bottom compression plates 222, 224 respectively. A continuous, flexible, liquid impermeable sidewall 226 (FIG. 10B) forms the sidewall and endwall of the bellows. The bellows has a spaced pair of opposing edges 228, 230 connected by the flexible endwall diaphragm, with one-way valves 231 in the face of the end wall diaphragm that allow liquid only into the bellows but not out. Alternatively, the endwall diaphragm could also be liquid impermeable and the one way valves 231 could be placed in the rigid compression plates 222, 224.

In the embodiment of FIG. 10A, a hinged pair of closely approximated edges 232, 234 have a series of one way valves along the hinged connection that allow liquid only out of the bellows. In FIG. 10A, expansion of the bellows draws liquid from a reservoir (not shown) into the matrix 220 through one way valves 231. Compression of the bellows expels substantially all or a portion of the liquid from the matrix through one way outlet 235.

In FIG. 10B, hinged edges 232, 234 are liquid tight, and liquid is instead expelled from the matrix 220 through one way exhaust valves 236 in the flexible end face of the bellows. Placing the inlet and outlet valves in the same face of the bellows provides a self-cleaning capability for the reactor. Any particles brought into the bellows will more likely be expelled through the outlet 236 instead of being trapped in the matrix as it travels to an outlet remote from the inlet.

The inlets and outlets 231, 236 in the embodiment of FIG. 10B can draw liquid in from and expel it out into a common reservoir. Alternatively, the inlets and outlets can be connected to separate inlet and outlet lines that communicate with the same or different reservoirs. Sequential synthetic reactions can be performed in the different reservoirs.

Process for Making Microbeads

The dynamic bed reactor can be used to simply adsorb adsorbates in liquid, or to promote enzymatic transformations or microbe mediated biochemical reactions. The efficiency of all of these processes can be enhanced by immobilizing adsorbents, enzymes or microbes in the matrix or by immobilizing them in beads that are in turn immobilized in the matrix of the dynamic bed reactor. The increase in efficiency is particularly notable with enzymes or microorganisms, particularly with the microbeads of the present invention which are small enough to reduce diffusional limitations in the bead. Substantially all the microbeads made by this process have diameters less than 50 microns, which has been found to greatly increase the efficiency of bioactive materials in the beads.

A device that can be used to produce these microbeads is shown in U.S. Pat. Nos. 3,758,033 and 3,240,253, which are incorporated by reference herein. These patents disclose sonic atomizing nozzles for use in making droplets of liquid, such as burner fuel. The present inventor has found that such nozzles can be used to manufacture the microbeads of the present invention with enzymes or microbes suspended in the beads.

This nozzle has remarkably been found not to damage the biological material passing through it, hence very sensitive materials, such as protoplasts and human tissue culture, can be immobilized in the very small beads. The present inventor has shown that bacteria which are atomized with such nozzles can produce twenty times as many colony forming units (CFU'S) as the same culture had before treatment, depending on the degree of aggregation. During production of the microbeads, additional compounds can be added to the encapsulation material. Examples of such additional compounds include a food source, trace nutrients, or density adjusting material.

A method of making the microbeads of the present invention is disclosed in Stormo and Crawford, "Preparation of Encapsulated Microbial Cells for Environmental Applications," Applied and Environmental Microbiology 58:727–730 (1992), which is incorporated by reference as fully as if it appeared herein.

EXAMPLE VIII

This example describes a method of producing large quantities of small beads of a consistent diameter less than 50 microns, more preferably less than 30 microns, that does not require separating and washing the prepared beads. High cell loadings (>50%, wt/vol) of virtually 100% active cells within beads 2 to 50 μm in diameter are possible.

Flavobacterium sp. strain ATCC 39723, a gram-negative aerobe that degrades a variety of chlorinated phenols such as pentachlorophenol (PCP), was grown in a defined mineral salts medium with sodium glutamate as the carbon and energy source. When cells reached mid-logarithmic phase, PCP (50 mg/liter) was added to induce the catabolic enzymes responsible for degradation of chlorinated phenols. When the PCP had been degraded, the cells were harvested by centrifugation.

Harvested cells were suspended at 20% (wet weight) per volume of either 2 or 4% sodium alginate (Sigma) in HEPES (N-2-hydroxyethylpiperazine-N'-2-ethanesulfonic acid) immobilization buffer, 1.5 to 5.0% molten agarose (Bethesda Research Laboratories) held at 45° C., or a pure polyurethane prepolymer. The polyurethane prepolymer was synthesized to minimize the release of carbon dioxide during the curing process once the prepolymer aerosol contacted an aqueous phase. It was prepared by reacting polyethylene glycol (100 meq of OH$^-$) with toluene diisocyanate (200 meq of cyanate) and various metabolizable carbon compounds (e.g., glucose or dextrin at 5 meq of OH$^-$) as the cross-linking agents.

Figure 11:
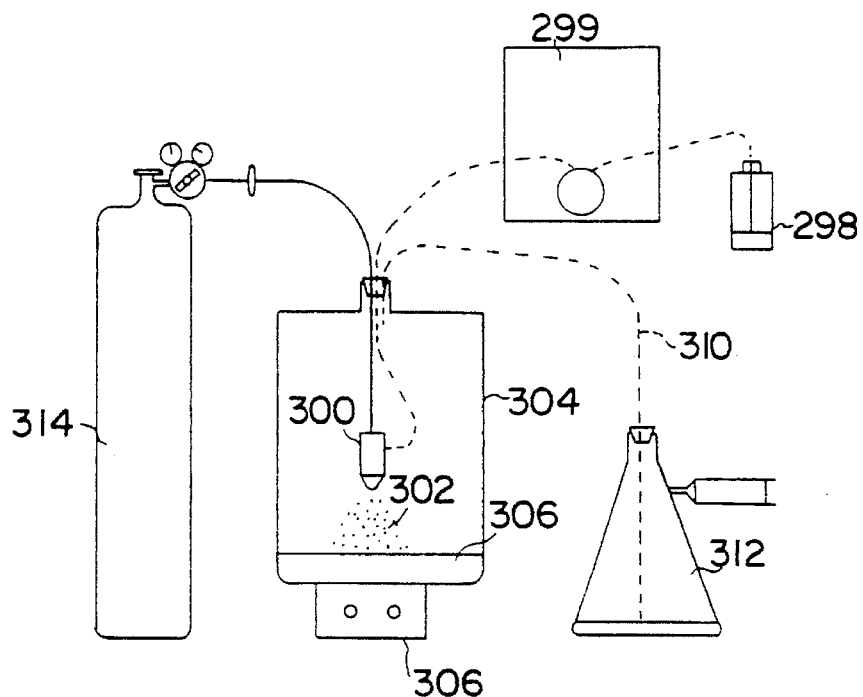
FIG. 11 is a schematic drawing of an apparatus for producing the microbeads of the present invention.
Figure 12:
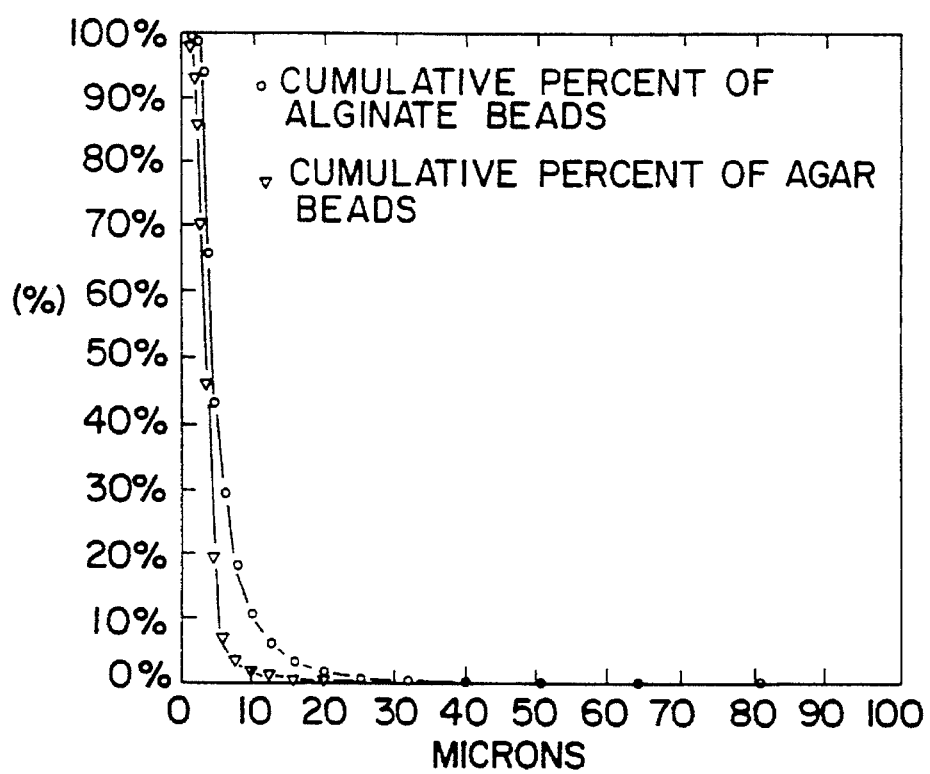
FIG. 12 is a graph showing bead size distribution by number of alginate and agarose beads produced by the apparatus shown in FIG. 11.
Figure 18:
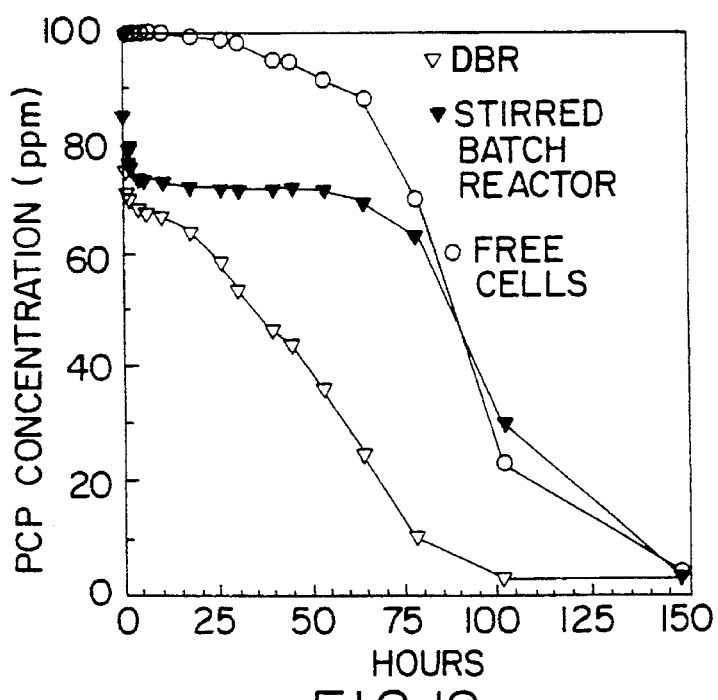
Figure 19:
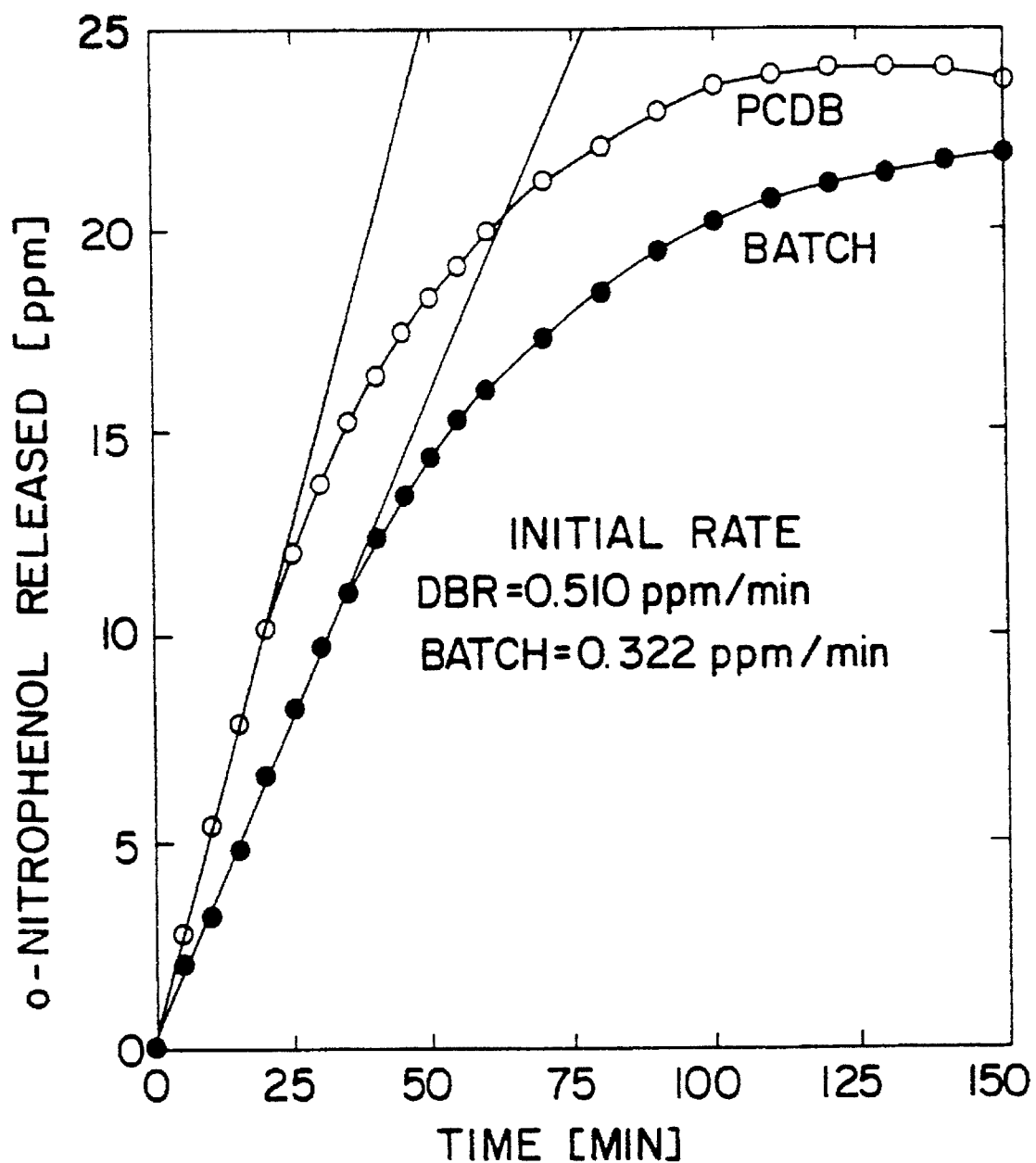
FIG. 19 is a graph comparing the hydrolysis of ONPG by immobilized enzymes in a batch reactor and the dynamic bed reactor of the present invention.

As shown in FIG. 11, cell suspensions in alginate or agar were pumped from a supply reservoir 298 with a peristaltic pump 299 through a low-pressure nozzle 300 (obtained from Sonic Development Corp., Parsippany, N.J. under product designation SDC NZZ 052HA nozzle and HS 303SS adapter) that passed through a rubber stopper and was arranged so that it introduced a fine aerosol 302 of cell suspension into a glass carboy 304 containing an aqueous phase 306 stirred with a magnetic stirrer 308. The apparatus was equipped with a vent tube 310 to exhaust nitrogen gas, and a trap 312 to remove any particles that passed out of the system in the exhaust phase. Gas pressures through the nozzle 300 were varied between 5 and 20 lb/in$^2$, with nitrogen gas supplied from a standard pressure bottle 314. The aqueous phase for the collection of microspheres was 50 mM $CaCl_2$ for the cells in alginate suspension or cold (4° C.) buffer for the cells in agarose or prepolymer suspensions.

In operation, gas was introduced into air port of the nozzle and the cell as described in the manufacturer's instructions. The cell suspension 298 was simultaneously pumped into the liquid inlet side port of nozzle 300. Small droplets of suspended cells were produced in aerosol 302, and were formed into microbeads as they entered the aqueous phase 306.

The low-pressure nozzle apparatus produced an aerosol of very small spheres (substantially all the beads being 2 to 50 μm in diameter) irrespective of the type of cell suspension passed through the system. The spheres of alginate polymerized into bacterium-loaded microbeads upon contact with the $CaCl_2$. The collected beads were acridine orange stained, and observation by epifluorescence microscopy showed that nearly all beads had stained cells inside. The polyurethane prepolymer polymerized into polyurethane microbeads upon contact and reaction with water. Typically, 23.5 ml of beads per 27.5 ml of suspension passed through the bead-making apparatus was produced. Bead sizes were determined with a multichannel Coulter Counter (model TA II; Coulter Electronics, Inc., Hialeah, Fla.) equipped with a population accessory that analyzed in 16 channels between 1.59 and 50.8 μm in diameter. The counter used a 140-μm orifice and was calibrated with 9.82-μm-diameter standard latex beads; 50% of the beads (by volume) were in size fractions of <20 μm in diameter.

Flavobacterium cells entrapped within the three types of microbeads retained high rates of biodegradation of PCP. Biodegradation of PCP in batch reactors containing free or immobilized cells was monitored by a spectrophotometric assay. By using simple batch reactors in triplicate, free cells and microencapsulated cells were compared at identical densities for their abilities to degrade 50 mg of PCP per liter in HEPES buffer with 500 mg of glutamate per liter. Flavobacterium sp. strain ATCC 39723 can degrade PCP as a sole source of carbon and energy, but its catalytic activities are greatly enhanced by the addition of a supplementary carbon source such as glutamate. The cells degraded PCP very rapidly when supplied with 500 mg of glutamate per liter. Unlike when large beads (2 to 3 mm in diameter) were used, rates were similar for both free and microimmobilized cells.

When buffer containing only PCP was employed, free cells exhibited long lag phases (up to 100 h). Encapsulation of the cells in agarose microbeads reduced the lag phase by about 25 h. Lag phases have always been observed in studies of PCP degradation by this Flavobacterium strain. Its underlying mechanism is not understood, but it probably reflects PCP toxicity. Oxygen limitation in our microbead preparations was not observed. Significant limitations were shown in previous work with much larger beads. The agarose-immobilized cells were quite stable and could be stored for many weeks at 4° C. without significant loss of biodegradative activity (data not shown). Similar results were observed for cells encapsulated in microbeads of alginate or polyurethane.

FIG. 12 shows that 90% of the alginate beads produced by this method are below 10 microns diameter, and that 98% of the agar microbeads are below 10 microns diameter. When comparing the distribution of bead sizes on a volumetric basis rather than a number basis, about 70% of the volume of both the alginate and agarose beads is in beads smaller than 35 microns diameter.

EXAMPLE IX

FIG. 17 is a bacterial degradation study in batch reactors. The Flavobacterium cells were immobilized in the polyurethane foam and washed to remove any free cells. Equal amounts of foam were added to either a dynamic bed reactor or a stirred reactor with equal volumes of buffer. Measurements of the PCP concentrations were measured in the reservoir by spectrophotometer readings at 320 nm. The initial 25–30% PCP removed is by binding to the foam, followed by degradation of PCP by bacteria. The much improved efficiency in the dynamic bed reactor is apparent, with about 80% removed in the dynamic bed reactor at 65 hours, while the stirred reactor was still at the 30% that was adsorbed initially.

FIG. 18 shows data obtained for a procedure as described in connection with FIG. 17. PCP concentration is measured as a function of time instead of % of PCP removed as in FIG.

17. FIG. 18 additionally includes data points for declining PCP concentration in the presence of the same amount of free cells that were added in the production of the polyurethane immobilized cells. The dynamic reactor results are affected by cells that were lost during foam immobilization and cells that were damaged by direct covalent bonding to the foam during the polyurethane polymerization reaction. In spite of this relative loss of cell mass in the dynamic reactor, the dynamic reactor had decreased the PCP concentration after 75 hours to about 10 ppm, while the free cells and the stirred reactor still had about 70 ppm of PCP at 75 hours.

EXAMPLE X

Many different reactions can be performed in the reactors of the present invention. Dehalogenation of lindane by a variety of porphyrins and corrins has been shown by Marks, et al. in *Applied and Env. Microb.* 55:1258–1261 (1989), which is also incorporated by reference. These metal ion-porphyrin complexes can be used in an organohalide detoxification system, for example by immobilization in a the compressible matrix of the present invention.

Chelating agents may also be used in the matrix, for example to chelate heavy metal. Biosorbents that chelate heavy metals, and which are suitable for incorporation into the matrix, are disclosed in *Biosorption of Heavy Metals*, Ed. Volesky, CRC Press, Boca Raton, Fla. (1989). Pages 318–319 and 330–335 of that book are incorporated by reference, and disclose metals and organisms that are suitable to adsorb them. Most biosorbents are dead cells, hence the matrix need not be biocompatible with them.

In other embodiments, oligonucleotides may be immobilized in the matrix to hybridize with DNA passing through the reactor that has complementary DNA sequences.

Further methods of biocatalyst immobilization in a matrix is discussed in *Ullmann's Encyclopedia of Industrial Chemistry,* Ed. Elvers, VCH Publishers, New York (1989), particularly at pages 4–5, 12–13, and 26–27, all of which are incorporated by reference. This reference discloses methods of physical adsorption, ionic binding of biocatalysts, chelate binding, and other techniques of immobilizing materials in the matrix As used in this specification, the term eH refers to an electrical or reducing potential, and is the negative log of the concentration of electrons in solution. The term "bioactive" means having a biological activity, or performing a biochemical synthetic or degradative function.

Having illustrated and described the principles of the invention in many preferred embodiments, it should be apparent to those skilled in the art that the invention can be modified in arrangement and detail without departing from such principles. We claim all modifications coming within the spirit and scope of the following claims.

I claim:

1. A method of transporting liquid through a reactive or adsorptive matrix, comprising the steps of:
    providing a resilient compressible open cell foam matrix, a reactive or adsorptive material within the matrix, and liquid in the matrix that contains a reactant or an adsorbate which undergoes a reaction in the matrix or is adsorbed in the matrix;
    compressing the foam matrix to expel substantially all of a first sample of liquid from the matrix; and
    allowing the resilient matrix to expand and draw a second sample of liquid into the matrix, wherein the liquid that is drawn into the matrix is substantially free of the liquid that was expelled from the matrix in the immediately preceding compressing step.

2. The method of claim 1 wherein the matrix contains a bioactive material selected from the group consisting of one or more of an enzyme and a biological cell.

3. The method of claim 1 wherein the foam matrix is in a first reactor, and the second sample of liquid is in a separate reservoir, and compressing the matrix expels at least 10% of the first sample of liquid out of the reactor, and allowing the resilient matrix to expand draws the second sample of liquid out of the reservoir into the reactor to expose the second sample of liquid to the reactive material.

4. The method of claim 3 wherein compression of the matrix expels at least about 75% of the first sample of liquid out of the bioreactor.

5. The method of claim 3 wherein the reservoir is a second reactor that performs a sequential biosynthetic step with the first bioreactor.

6. The method of claim 1 wherein the foam matrix is pulsed at a frequency of at least one cycle per second.

7. The method of claim 1 wherein the foam matrix is pulsed at a frequency of as long as about one cycle per hour.

8. The method of claim 1 wherein the foam matrix is a polyurethane foam.

9. The method of claim 1 wherein the reactive or adsorptive material is covalently or ionically attached to the open cell foam.

10. The method of claim 1 wherein the reactive material is entrapped in beads, a pore size of the matrix and a size of the beads being sufficient to physically entrap the beads in the matrix.

11. The method of claim 10 wherein substantially all of the beads have a diameter less than about 50 microns.

12. The method of claim 11 wherein the beads are formed by distributing the reactive material in an immobilization material having a viscosity greater than about 100 cp, and forming the resulting material into droplets which form the microbeads wherein at least 99 percent of the total number of microbeads formed are less than 50 microns in diameter.

13. The method of claim 11 wherein the microbeads are formed without oil immersion or interfacial polymerization by distributing the reactive or adsorptive material in an immobilization material having a viscosity greater than 100 cp, wherein the reactive or adsorptive material and the immobilization material are mixed into a mixture and the mixture is formed into droplets by exposing the mixture to ultrasonic acoustic energy, and subsequently solidifying the droplets to form the bead.

14. The method of claim 1 wherein the reactive or adsorptive material is covalently or ionically attached to the foam matrix.

15. The method of claim 1 wherein the foam matrix comprises a polymerizable material, and the reactive or adsorptive material is retained in the matrix by polymerizing the material of the matrix in the presence of the reactive or adsorptive material.

16. The method of claim 1 further comprising the step of sensing in the first sample of the liquid, as the first sample of the liquid is expelled from the foam matrix, a physical property related to an efficiency of a desired reaction.

17. The method of claim 16 wherein the physical property is selected from the group consisting of pH, eH, nutrient concentration, a reactant concentration, and a product concentration.

18. The method of claim 16 further comprising the step of comparing the pH of the liquid as it is expelled from the foam matrix to an optimum pH of the reactive material, and adjusting the pH if the pH differs from an optimum pH for the reactive material.

19. The method of claim 1 wherein the liquid comprises a reactant or adsorbate, and the reactive material comprises a material selected from the group consisting of one or more of an adsorptive material, an enzyme that transforms the reactant, and a biological cell that transforms the reactant.

20. The method of claim 19 wherein the reactant or adsorbate is held in a reservoir and the foam matrix is in a separate reactor, and the step of compressing the foam matrix expels substantially all liquid from the bioreactor into a receptacle, and the step of allowing the matrix to expand feeds a process liquid from the reservoir into the reactor without an auxiliary pump to move the liquid from the reservoir to the reactor.

21. The method of claim 20 wherein the receptacle is the reservoir.

22. A method of transporting liquid through a bioactive or adsorptive matrix, comprising the steps of:
    providing an upstream reservoir vessel with a supply of liquid comprising a xenobiotic;
    providing a bioreactor vessel which defines an enclosed space having a cross section, the bioreactor having an upstream inlet and a downstream outlet, and an open cell polyurethane foam matrix positioned inside the space with bioactive and adsorptive material in the matrix, and a piston member having a solid compression member across the cross section wherein the piston is capable of periodically moving to compress the matrix without allowing liquid to move out of the foam matrix in an upstream direction;
    periodically compressing the foam matrix with the piston to form a compressed foam matrix and move liquid out of the compressed foam matrix in a downstream direction without moving the liquid in an upstream direction; and
    periodically expanding the compressed foam matrix to draw a process liquid from the upstream reservoir into the foam matrix.

23. A method of transporting liquid through a reaction matrix, comprising the steps of:
    periodically compressing an open cell foam reaction matrix to expel a reaction liquid from the foam matrix in a downstream direction but not an upstream direction; and
    periodically expanding the open cell foam reaction matrix to draw a process liquid into the matrix from an upstream direction but not a downstream direction, and allowing the liquid to remain in contact with the foam matrix a sufficient period of time for a desired reaction to occur.

24. A method of transporting liquid through a reactive or adsorptive matrix, comprising the steps of:
    periodically compressing an open cell foam reaction matrix to expel substantially all of a reaction liquid from the foam matrix; and
    periodically expanding the open cell foam reaction matrix to draw a liquid into the matrix, wherein the liquid that is drawn into the matrix is substantially free of liquid that was expelled from the foam matrix in an immediately preceding compression.

25. The method of claim 24 wherein the matrix is suspended in a process liquid, and a sufficient period of time is allowed to elapse between a compression and a subsequent expansion of the matrix that substantially all liquid expelled from the matrix during the compression moves away from the matrix and is replaced by process liquid that was not expelled from the matrix during the preceding compression.

26. A method of transporting liquid through a reaction matrix, comprising the steps of:
    periodically compressing an open cell foam reaction matrix, which has an upstream and a downstream face, to expel a reaction liquid from the foam matrix in a downstream direction through the upstream face of the matrix, without drawing liquid in through the downstream face;
    periodically expanding the open cell foam reaction matrix to draw liquid into the matrix in an upstream direction, and through the downstream face of the matrix, without drawing liquid in through the upstream face.

27. A method of transporting liquid through a bioactive matrix, comprising the steps of:
    providing a pulse flow reactor comprising a syringe pump with a reciprocable piston and a compressible chamber, and a unitary open cell polyurethane foam matrix filling the chamber, wherein the polyurethane foam contains a bioactive organism;
    providing a valve that allows liquid in the chamber to flow only through an outlet line from the chamber when the chamber is compressed, and flow only through an inlet line into the chamber when the chamber is expanded;
    providing a reservoir upstream from the syringe pump, wherein the reservoir contains a substance to be acted on by the bioactive organism; and
    reciprocating the piston to compress the chamber and expel liquid out of the matrix, through the valve into the reservoir, and sequentially expand the chamber to draw liquid into the syringe pump from the reservoir by a relative vacuum created by expansion of the chamber.

28. The method of claim 27 further comprising the step of sampling a pH of the liquid in the outlet line as it is expelled from the matrix and before it reaches the reservoir, and adjusting the pH of the matrix to an optimum pH if the pH of the liquid in the outlet line differs from the optimum pH.

* * * * *